(12) United States Patent
Van Meter et al.

(10) Patent No.: US 6,944,485 B1
(45) Date of Patent: Sep. 13, 2005

(54) HYPERBARIC RESUSCITATION SYSTEM AND METHOD

(76) Inventors: Keith W. Van Meter, 17 Carriage La., New Orleans, LA (US) 70114; Frederick A. Kriedt, 560 Lynnmeade Rd., Gretna, LA (US) 70056

( * ) Notice: Subject to any disclaimer, the term of this patent is extended or adjusted under 35 U.S.C. 154(b) by 0 days.

(21) Appl. No.: 10/019,548

(22) PCT Filed: Apr. 20, 2000

(86) PCT No.: PCT/US00/10968

§ 371 (c)(1),
(2), (4) Date: May 16, 2002

(87) PCT Pub. No.: WO01/80934

PCT Pub. Date: Nov. 1, 2001

(51) Int. Cl.[7] .............................................. A61B 5/00
(52) U.S. Cl. ...................................... 600/310; 600/326
(58) Field of Search ................................ 600/310, 322, 600/323, 326, 473; 356/300, 319, 320

(56) References Cited

U.S. PATENT DOCUMENTS

| | | |
|---|---|---|
| 4,281,645 A | 8/1981 | Jöbsis |
| 4,805,623 A | 2/1989 | Jöbsis |
| 5,242,602 A * | 9/1993 | Richardson et al. ........ 356/300 |
| 5,251,632 A | 10/1993 | Delpy |
| 5,309,921 A | 5/1994 | Kisner et al. |
| 5,313,941 A | 5/1994 | Braig et al. |
| 5,685,313 A | 11/1997 | Mayevsky |
| 5,873,821 A | 2/1999 | Chance et al. |
| 5,879,294 A * | 3/1999 | Anderson et al. ........... 600/310 |
| 6,283,123 B1 | 9/2001 | Van Meter et al. |

FOREIGN PATENT DOCUMENTS

SU    395091    12/1973

OTHER PUBLICATIONS

Hempel et al., "Oxidation of Cerebral Cytochrome aa3 by Oxygen Plus Carbon Dioxide at Hyperbaric Pressures," J. Applied Physiology: Resp., Env., and Exercise Phys., vol 43, No. 5, Nov. 1977.

Brown et al., "In Vivo Binding of Carbon Monoxide to Cytochrome C Oxidase in Rat Brain," J. Applied Physiology, vol. 68, No. 2, Feb. 1990.

* cited by examiner

Primary Examiner—Eric F. Winakur
(74) Attorney, Agent, or Firm—Garvey, Smith, Nehrbass & Doody, L.L.C.; Seth M. Nehrbass

(57) ABSTRACT

A hyperbaric resuscitation system (10) includes a hyperbaric chamber (20) having a volume sufficient to enclose a human patient (1) and at least two operating personnel (60). The system (10) also includes a device for pressurizing the hyperbaric chamber (20) to at least 1.5 atmospheres with air. The concentration of oxygen in high pressure, oxygen-rich gas to be breathed by the patient (1) provided by an independent system (41) at chamber pressure is automatically regulated by a regulating system (33) which receives information about the amount of oxygen in cerebral tissue of the patient (1) from a spectrophotometer (51, 52). Although devices for measuring the exact amount of oxygen in cerebral tissue do not yet exist, the presently available devices can show trends in the amount of oxygen in the tissue. Since the physician working on a patient in a hyperbaric resuscitation system is more concerned about trending than exact values, the present system can still be of great benefit in resuscitating patients.

22 Claims, 23 Drawing Sheets

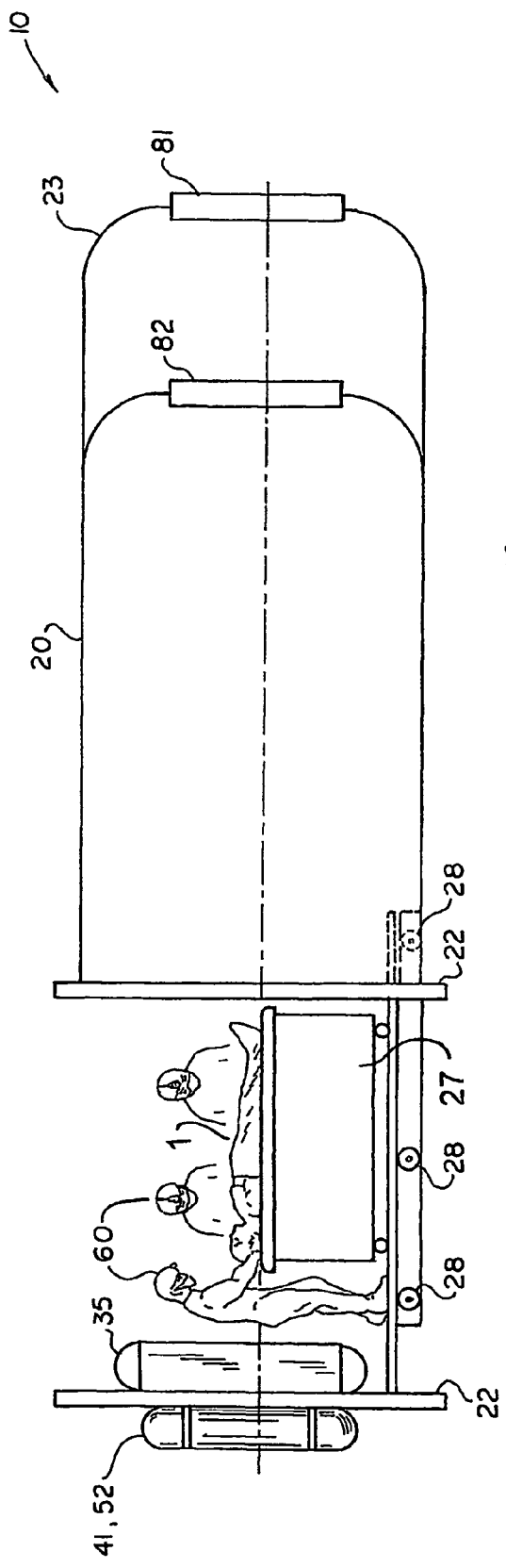
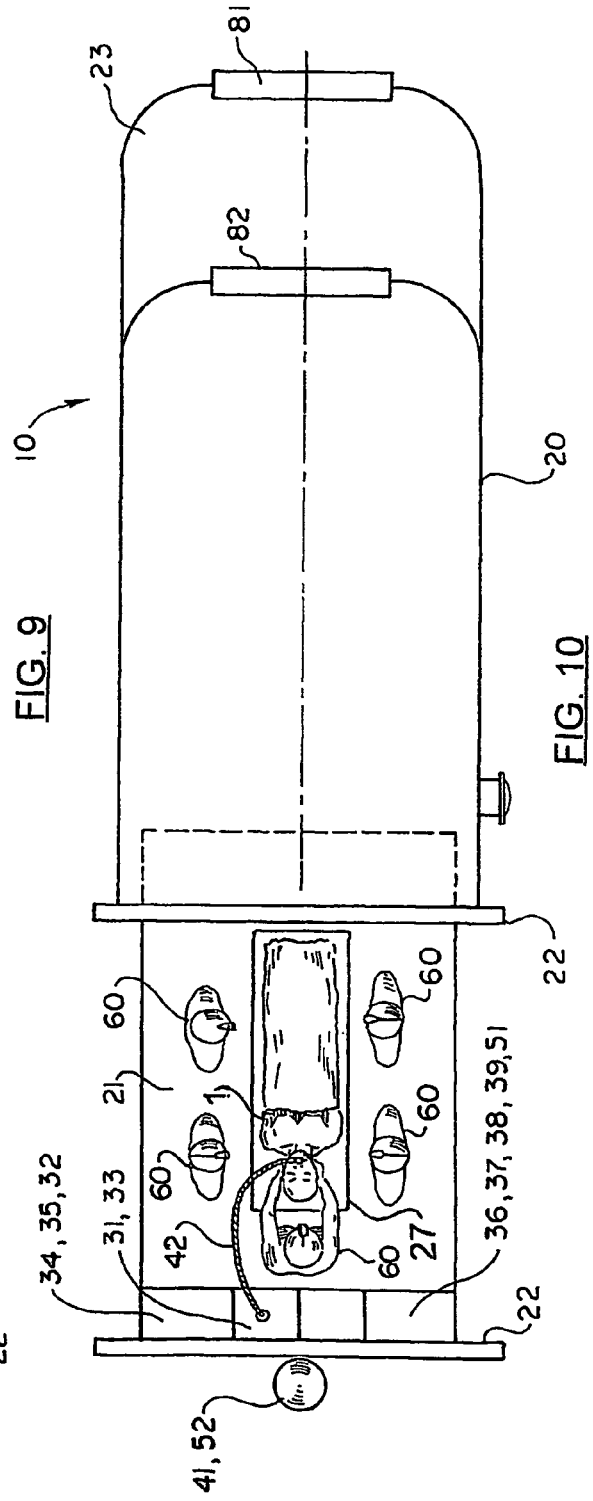
FIG. 9
FIG. 10

HYPERBARIC RESUSCITATION SYSTEM AND METHOD

CROSS-REFERENCE TO RELATED APPLICATIONS

Incorporated herein by reference are the following patent applications: co-pending U.S. patent application Ser. No. 09/108,464, filed 1 Jul. 1998, which is a continuation-in-part of U.S. patent application Ser. No. 08/812,368, filed 5 Mar. 1997, which is a continuation-in-part of U.S. patent application Ser. No. 08/348,555, filed 1 Dec. 1994.

STATEMENT REGARDING FEDERALLY SPONSORED RESEARCH OR DEVELOPMENT

Not applicable

REFERENCE TO A "MICROFICHE APPENDIX"

Not applicable

BACKGROUND OF THE INVENTION

1. Field of the Invention

The present invention relates to hyperbaric chambers and medical treatment methods and systems using hyperbaric chambers. More particularly, the present invention relates to a system and method for using a hyperbaric chamber, a spectrophotometer (preferably a NIRoscope), and an automatic regulating device which receives information from the spectrophotometer to increase the amount of oxygen which gets to the brain of a patient being resuscitated after suffering from, for example, myocardial infarction or cerebral ischemia. The NIRoscope can also be used independently in critical care to monitor $aa_3$ redox ratio or even be broadened to other chromophores in the brain in conjunction with neurology and mental health.

2. General Background of the Invention

Shrinking health care dollars have made the medical profession acutely aware of the enormous cost associated with successful cardiopulmonary resuscitations. (1,2—the parenthetical reference numerals indicate the appropriate article listed in the Appendix). The major expense is related to post-resuscitative care in the hospital, especially the time spent in intensive care. Cost per resuscitation depends on the percentage of survival to hospital discharge and ranges from $550,000 for 0.2% survival to $110,000 for a 10% survival. From a cost analysis perspective, it would be extremely beneficial if the number of survivors could be increased, if their post-resuscitation condition still permitted them to function as independently as possible, and if the post-resuscitation time they spent in the intensive care unit was markedly reduced. For example, it has been shown that by raising the resuscitation success ratio from the present 12% to 20%, there could be a cost savings of approximately $40,000 per patient. (2) According to Virtis (1), of the 3,308,000 patients hospitalized annually, about 1% (330,800) experienced cardiac arrest and were administered CPR. If the current success rate of 12.8% (3) could be raised to 20%, a national health care cost savings of $1.32 billion ($40,000×330,000) per year could be realized.

Although oxygen is considered to be the most important drug used in resuscitation from cardiopulmonary arrest, it is disheartening to learn that for the past 30 years there has been little improvement in resuscitative techniques and that advances in oxygen delivery have not been incorporated to any meaningful extent in resuscitation.

Currently, there are at least two major limitations associated with conventional oxygen delivery: the first pertains to methods of oxygen administration and the second pertains to the unavailability of a reliable, non-invasive, direct or indirect cerebral cortical oxygen monitor that could help assure adequate oxygenation of the brain during CPR. Even under ideal conditions, neither masks nor endotracheal tubes—the techniques currently used for delivering oxygen during resuscitation—deliver sufficient oxygen at sea level (1 atmosphere absolute (atm abs)) for adequate, let alone optimum, oxygen delivery. Therefore, maximum benefit, i.e. maximum recovery of cerebral neurons (minimum residual brain damage) is not attained and, thereby, represents the preeminent reason for the aforementioned dismal results with respect to minimizing brain damage following resuscitation from cardiopulmonary arrest.

What is needed is a system that will provide sufficient oxygen delivery and a sensor for non-invasively measuring in real-time the adequacy of oxygen delivery to the cortical neurons. Hyperbaric oxygen (HBO) provides the means whereby sufficient oxygen could be delivered to the patients. HBO increases the amount of oxygen physically dissolved in the plasma to an extent that greatly supplements that which is carried by hemoglobin in the red blood cells. More importantly, HBO provides for a high partial pressure of oxygen—greater than that which could be attained at sea level—which increases the rate of diffusion of the oxygen into the tissues and cells and helps assure sufficient oxygen to overcome hypoxia and maintain cellular metabolism and integrity. It is this state of oxidative metabolism that lends itself to non-invasive measurement and, thereby, by inference, of adequate tissue and cellular oxygenation. Oxygen also exerts other beneficial physiologic-pharmacologic effects which will prevent or ameliorate the onset of hypoxia-induced cerebral and cardiac pathology.

Increasing the partial pressure of oxygen inhaled during resuscitative procedures (pressures of oxygen that can be obtained only by hyperbaric oxygen therapy (HBOT)) is expected to be pivotal in improving the success ratio of resuscitation. Such anticipation is to be expected because of the documented beneficial effects of HBOT:

1. HBOT has been suggested as an indicator for identifying potentially good resuscitative candidates. Holbach (4) reported that if patients with cerebral ischemic damage responded well to an initial exposure to HBOT they would continue to improve during post-resuscitative efforts. Patients who did not respond well to the initial HBOT exposure were less likely to recover from ischemic damage.
2. Even after extended periods of cerebral ischemia, resuscitation may be improved by HBOT (5,6)
3. HBOT, when used in conjunction with single photon emission computed tomography (SPECT) (7, 8) using an appropriate radioactive tracer has been shown to help detect the extent of brain injury, identify if there is potentially recoverable brain tissue, and help identify the endpoint of therapy. HBOT is absolutely essential for recovering these neurons.

To effect successful resuscitations the oxygen dosage must be optimized. Holbach et al. reported that injured brain responds differently to increased pressures of oxygen than does non-injured brain. These investigators demonstrated, based on regional energy utilization, that 1.5 atmospheres absolute (atm abs) of oxygen is optimum for treating injured brain. However, Holbach was not working with resuscitation procedures in which developing and maintaining sufficient cerebral perfusion is critical for delivering oxygen and nutrients to the neurons and for removing end products of metabolism if a successful resuscitation is to be effected.

In injured brain there may be damage to the cerebral circulation thereby disrupting cerebral perfusion. The major limitation of conventional cardiopulmonary resuscitation is the failure to be able to attain and maintain a sufficient cerebral perfusion so as to sustain cardiac and neuronal function.

HBOT represents the most efficient means of supplying sufficient oxygen to tissues (neurons in the brain) thereby reversing hypoxia, sustaining neuronal metabolism, quenching free radicals, decreasing the local formation of acidosis, and stimulating angiogenesis (9). There is no drug currently available that can do what oxygen does in enhancing the survival of injured neurons (10).

It is the contention of the present inventors that real-time monitoring of cellular oxidative states, an indirect but more meaningful measure of tissue oxygen tensions, would help predict whether salvageable tissues are present. Indeed, Sheffield showed that measuring tissue oxygen tensions has been used successfully as a means for predicting which problem wounds would respond to HBOT. Not only does this technique provide predictive value, it also permits following the course of therapy so as to gauge the efficacy of the therapeutic recovery techniques. Thus, from a comparative perspective with respect to the brain, measuring cerebral partial pressure of oxygen ($PO_2$) during resuscitation would be an excellent gauge of successful resuscitative efforts. Waxman et al. used the $PO_2$ in the muscles of the upper arm to judge the success of resuscitation from hypovolemic shock (10). Rivers (11) measured cardiac venous $PO_2$ to predict the return of spontaneous circulation while McCormick (12) measured cerebral venous $PO_2$ to gauge recovery of comatose patients in intensive care. Unfortunately, no one has yet determined what is the real-time, optimal cerebral oxygen tension for tissue recovery, nor does anyone know, using current technology, how to assure that there is optimal oxygen delivery during resuscitation.

Although cerebral neurons are extremely vulnerable to hypoxia, irrespective of its etiology, there have been no reports of direct measurements of cerebral neuronal oxidative states as a means for predicting success of resuscitative efforts. One of the most important reasons for the lack of such knowledge is the absence of reliable, non-invasive instrumentation for measuring cerebral neuronal oxidation-reduction states in humans.

Based on a review of the literature, the present inventors have come to believe that the most promising approach for the non-invasive measurement of cerebral oxidation-reduction states (cerebral $PO_2$) in humans is one based on near infrared (NIR) spectroscopy. Measuring the ratio of cerebral arterial and venous hemoglobin using NIR spectroscopy has been accomplished while individuals were breathing air under 1 atm abs conditions. However, this technology cannot be used under HBOT conditions because the hemoglobin in both the arterial and venous circulations may be completely saturated with oxygen. Instrumentation for measuring the in vivo cytochrome oxidase redox ratio was used successfully in bloodless small animals. (13, 16) However, attempts to apply this technology to blood-profused large animals and humans, Matcher provided inconsistent results. It has been reported the failure to obtain consistency was due to the requirement for a higher gain to detect the cytochrome oxidase redox ratio—there is less cytochrome oxidase than hemoglobin per unit volume of brain tissue and its NIR absorption signal is weaker. It appears that one of the basic problems to be overcome in applying NIR spectroscopy as an aid in resuscitating adult humans is to be able to measure the relatively weak cytochrome oxidase absorption in the presence of a pulsating hemoglobin signal that is 10 times stronger. The effects of varying Hb absorbance, water concentration and tissue light scattering have led to questionable results. (20, 21).

One desideratum for improving resuscitative efforts is a non-invasive instrument with sufficient sensitivity to measure the adequacy of tissue oxygen delivery in real-time at the cellular level so that attending physicians could optimize resuscitative efforts. Such techniques do not have to be quantitative since it is the relative changes in redox levels in real-time that are important.

Recent advances in spectroscopy have made it feasible for appropriate instrumentation to be developed. For example, charged couple device (CCD) spectrophotometers have become more sensitive and can provide absorbance spectra with integration time ranging from 10 msec to 10 seconds. This alone may be adequate to monitor aa3. If not, based on mathematical models using Fourier Transform and deconvolution methods in conjunction with data obtained from a CCD in the near infrared range, the present inventors concluded that an even more sensitive spectrophotometer could be built. In fact, by applying the inventors' algorithm to synthetic (but realistic) cerebral cortex absorption spectra, the redox ratio of cytochrome oxidase can be extracted from the spectra. Furthermore, the result of this analysis shows the real component of the Fourier Transform to be linear to the cytochrome oxidase redox ratio to the fifth decimal place. Such sensitivity should provide the basis for designing instrumentation that is needed for making the necessary measurements of oxidized-reduced cytochrome oxidase ratios in real-time during cardiopulmonary resuscitation. This same technique may be applied to other natural chromophores in the brain such as neuron transmitters or treatment drugs in conjunction with the diagnostics treatment of neurology and psychiatry.

Hyperbaric chambers have long been used for increasing the amount of oxygen supplied to patients suffering from oxygen deprivation. Several articles and patents address this subject. However, it is important to supply the proper amount of oxygen to a patient. Supplying too much can be almost as harmful as supplying too little.

U.S. Pat. Nos. 3,688,770, 3,877,427, and 3,547,118 disclose hyperbaric chambers for oxygenating blood. In U.S. Pat. No. 3,547,118, a regulator automatically controls the relationship between the pressure of the chamber and the pressure of the oxygen supply of a patient in the chamber. U.S. Pat. No. 4,582,055 discloses a similar system.

U.S. Pat. No. 5,220,502 discloses a system for automatically measuring the blood pressure of a patient in a hyperbaric chamber.

U.S. Pat. Nos. 4,281,645; 5,313,941; and 5,873,821 disclose spectrophotometers.

U.S. Pat. Nos. 3,984,673, 4,448,189, and 4,633,859, disclose various apparatus for controlling the environment in hyperbaric chambers.

See also Dalago et al., SU patent document no. 395,091, December 1973; F. G. Hempel et al., "Oxidation of cerebral cytochrome aa3 by oxygen plus carbon dioxide at hyperbaric pressures,": J. Applied Physiology: Resp.; Env., and Exercise Phys., Vol. 43, No. 5 (November 1977); and S. D. Brown et al., "In vivo binding of carbon monoxide to cytochrome c oxidase in rat brain," J. Applied Physiology, Vol. 68, No. 2 (February 1990); and U.S. Pat. No. 5,251,632.

All references mentioned herein (and all references to which they refer) are hereby incorporated herein by reference.

BRIEF SUMMARY OF THE INVENTION

The present invention is a hyperbaric resuscitation method and system including a hyperbaric chamber and a spectrophotometer; the system includes means for automatically regulating the amount of oxygen in the gas breathed by the patient by regulating the oxygen concentration and pressure of the breathed gas using information from the spectrophotometer.

The method of the present invention comprises placing a patient in a hyperbaric chamber having a volume sufficient to enclose a human patient and at least two operating personnel, pressurizing the hyperbaric chamber to greater than existing barometric pressure (preferably to at least 1.5 atmospheres), providing oxygen-rich gas to be breathed by the patient via a previously placed endotracheal tube, pressurizing the oxygen-rich gas to a pressure similar to that of the hyperbaric chamber, and monitoring oxygen in cerebral tissue of the patient with a non-invasive monitoring means. The method preferably also includes the step of automatically regulating the concentration of oxygen in the oxygen-rich gas supplied to the patient via endotracheal tube in response to readings of the non-invasive monitoring means. The operating personnel breathe chamber air which is not oxygen rich.

The present invention comprises a device, the use of which will assist in real-time evaluation of the efficacy of advanced cardiac life support (ACLS) resuscitation procedures. Specifically, the present invention comprises a near infrared sensor (NIRoscope) capable of non-invasively measuring real-time changes in the oxidation-reduction (redox) states of cytochrome oxidase in the cerebral cortex of patients (adults and children) undergoing emergency cardiopulmonary resuscitation in an hyperbaric environment. The real-time changes in redox states will be used immediately by the attending physician to assess the efficacy of their resuscitative efforts and to help direct changes so as to optimize the ACLS procedures for the individual patients. The net result of these efforts should be an enhancement of procedure efficacy thus helping to assure patient survival. In addition, successful application of NIRoscope-assisted resuscitation procedures should also result in the preservation of as much functional brain tissue as possible thereby yielding an increase in patients' self-reliance and a decrease in the length of time patients are required to stay in the intensive care unit at the hospital.

As procedures are developed and stabilized, an additional improvement would be to remotely treat the patient from outside the chamber and lock in medical personnel if complications arise.

The present invention comprises a NIRoscope capable of measuring a cytochrome oxidase redox near infrared (NIR) signal with a 0.1 optical density (OD) unit total range with a 0.005 OD sensitivity in a pulsating 1.0 OD hemoglobin NIR signal. To test the present invention, measured accuracy will be evaluated by processing existing spectrum from rats, a human forearm and piglets, along with collected data from adolescent swine, adult humans and comparing the inventors' algorithm with the presently used multi-component analysis algorithms available today. Results will be compared to determine which data processing method is superior. Testing of the instrument on an existing, on-going, acute swine model will occur at an institute under normal atmospheric and hyperbaric conditions. This testing will establish the accuracy, safety and effectiveness of the instruments by invasive techniques. Once accuracy and safety have been established, the instrument will be utilized to conduct research at a major trauma center, recording the redox ratio of cytochrome oxidase in patients undergoing emergency resuscitation. At the same time another like instrument will be incorporated into swine model resuscitation experiments on-going at the same institution. Further testing would involve a controlled human trial of resuscitation using a NIRoscope-assisted resuscitation in an hyperbaric environment.

It is an object of the present invention to provide an integrated system for non-invasively measuring cerebral neuronal oxidation-reduction states during cardiopulmonary resuscitation in an hyperbaric environment.

It is another object of the present invention to provide a NIRoscope and a new mathematical method that is used to enhance the instrument's sensitivity and ability to measure, in real-time, the change in the redox state of patients undergoing resuscitation. The NIRoscope will be tested in an existing acute animal resuscitation model and in a chronic extension of this model. Shortly thereafter, a NIRoscope will be used in a clinical setting to measure the changes in cerebral redox states during presently on-going ACLS-approved human resuscitation. It is during this preliminary clinical test that techniques for attaching the NIRoscope to the patient will be refined and knowledge will be increased about the redox behavior of the cytochrome oxidase during resuscitation. Later, a clinical study comparing standard human resuscitation with hyperbaric resuscitation will be performed.

It is also an object of the present invention to provide a resuscitation method and system including a hyperbaric chamber and a spectrophotometer;

It is a further object of the present invention to provide a resuscitation method and system including means for automatically regulating the amount of oxygen in the gas breathed by the patient by regulating the oxygen concentration and pressure of the breathed gas using information from the spectrophotometer;

It is another object of the present invention to provide a hyperbaric resuscitation system comprising a hyperbaric chamber having a volume sufficient to enclose a human patient and at least two operating personnel, means for providing oxygen-rich gas through an endotracheal tube to be breathed by the patient, pressurizing means for pressurizing the hyperbaric chamber (preferably to at least 1.5 atmospheres) and for pressurizing the oxygen-rich gas to a pressure similar to that of the hyperbaric chamber, a spectrophotometer for monitoring oxygen in cerebral tissue of the patient, and regulating means for regulating the concentration of oxygen in the oxygen-rich gas in response to readings of the spectrophotometer.

It is another object of the present invention to provide a resuscitation method comprising an unmanned hyperbaric chamber sufficient to enclose one human patient, a means for providing oxygen rich gas to be breathed by the patient via an endotracheal tube with all ACLS devices placed and fixed to the patient before pressurization which can be operated from outside the hyperbaric chamber.

It is another object of the present invention to utilize the Niroscope's ability to non invasively monitor cerebral cortical changes in hemoglobin, water and the redox state of cytochrome oxidase, independent and without the use of HBO. The ability to observe the previous mentioned changes with the Niroscope is expected to enhance the art and science of medicine where cellular respiration is or has been impaired. Examples include the following: in neurological rehabilitation centers as a guide for improving cerebral function after local cerebral damage due to stroke, trauma, or exposure to toxic or anoxic encephalopathies, in the operating room as a guide for evaluating cerebral oxygenation status during surgery where cerebral blood flow has been compromised i.e. bypass surgery, percutaneous transluminal coronary angioplasty, or endarterectomy; in evaluating cerebral hemodynamics and oxygen utilization in fetal and neonatal brains as a guide for detecting and managing hypoxic/anoxic states irrespective of etiology; in organ donation as a guide for improved management of brain-dead organ donors; and in any area of research requiring non-invasive monitoring of changes in the function of the respiratory chain (12). It is another object of the invention to measure the change of absorbance spectra for any natural or synthetic chromophore that exist or is introduced in the brain. Examples of natural chromophores would be any neurotransmitter that has an absorbance peak in the 600–1050 nm range. An example of a synthetic drug would be any neurologic or psychiatric drug (lithium) that would be used by a neurologist or psychiatrist. The technique would be to establish a baseline at some certain point and monitor the change in absorbance spectrum after a given time based on patient symptoms. Symptom and absorbance spectra could be correlated by the attending physician.

BRIEF DESCRIPTION OF THE SEVERAL VIEWS OF THE DRAWINGS

For a further understanding of the nature, objects, and advantages of the present invention, reference should be had to the following detailed description, read in conjunction with the following drawings, wherein like reference numerals denote like elements and wherein:

FIG. 3 is 0% oxidized cytochrome oxidase, FIG. 4 is 50% oxidized cytochrome oxidase, and FIG. 5 is 100% oxidized cytochrome oxidase. The axis of abscissa is wavenumber (N) in 1/nanometer and the axis of ordinates is the Fourier coefficient (Fo). Notice that the only component that is changing is the real component of the Fourier transform. It was found to be linear to the fifth significant place (see FIG. 6).

FIGS. 9 and 10 are side and top views, respectively, of the preferred embodiment of the apparatus of the present invention.

PARTS LIST

Figure 1:
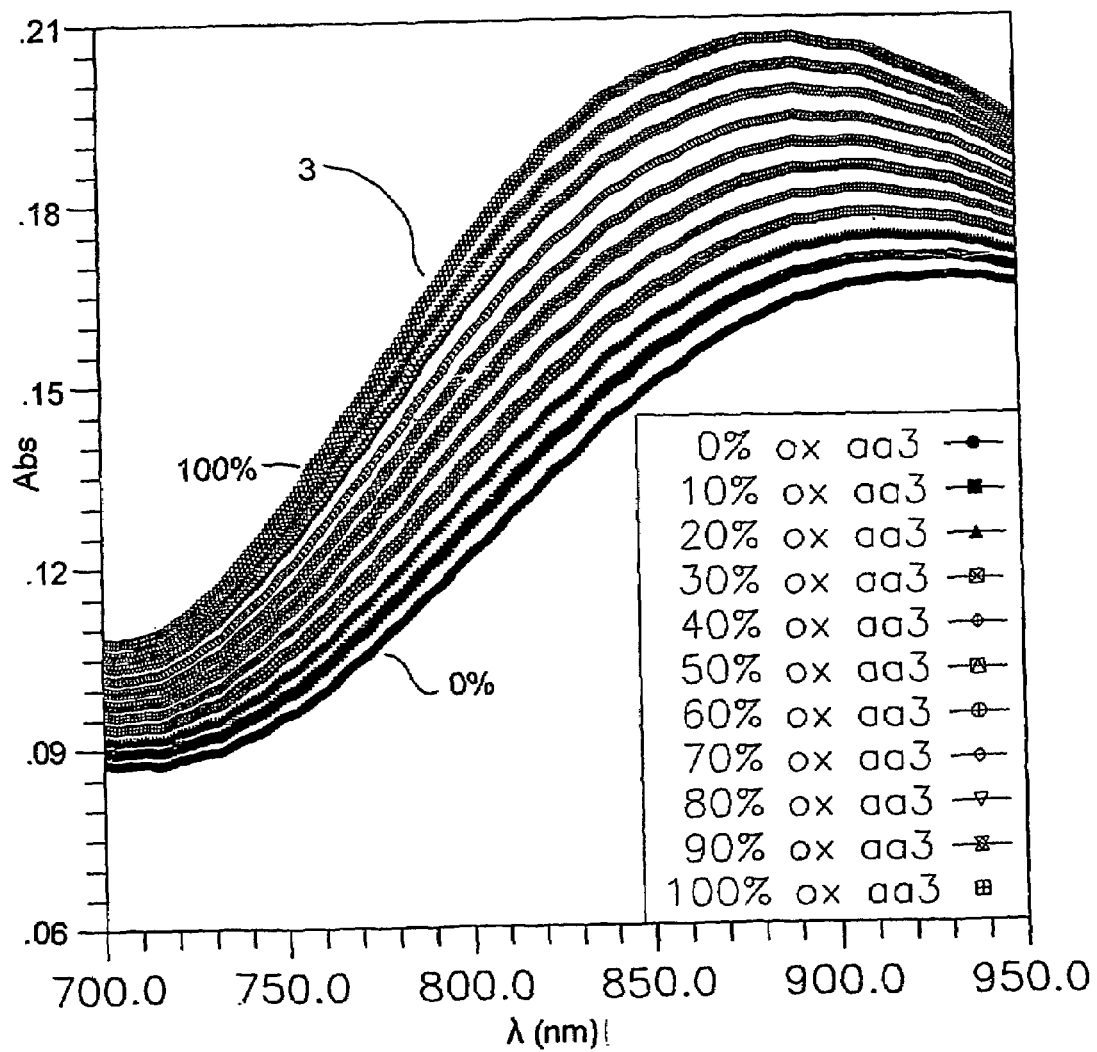
FIG. 1 shows theoretical absorption spectra excluding water expected to be found during evaluation of an adult human. The axis of abscissa is wavelength (A) in nanometers, and the axis of ordinates is absorbance (Abs) in optical density. These curves were computer generated using published extinction coefficients in the near infrared range (Wray 1987), concentrations typically found in the brain (Cope 1988) and based on the fact that the path lengths are equal in all cases, allowing a 1 cm. value to be assumed. Each curve represents 100% oxygenated hemoglobin (hyperbaric conditions) and various percentages of oxidized cytochrome oxidase from 0% (bottom curve) to 100% (top curve).

The following is a list of suitable parts and materials for the various elements of the preferred embodiment of the present invention.

1 patient
2 patient's head
3 calculated spectrum of predicted absorbance found in a human head
4 curve of the magnitude of the Fourier transform of the absorbance spectrum versus wave number
5 spectrum 3 with DC component removed
6 curve of the real component of the Fourier transform of the absorbance spectrum versus wave number
8 curve of the imaginary component of the Fourier transform of the absorbance spectrum versus wave number
9 curve of the real component of the Fourier transform (FoR) of the absorbance spectrum versus percentage of cytochrome oxidase (% ox aa3)
10 hyperbaric resuscitation system (directed patient access) of the preferred embodiment of the present invention
20 multiplace hyperbaric chamber
21 rolling cart in hyperbaric chamber 20
22 quick-opening closure of hyperbaric chamber 20
23 outer lock of hyperbaric chamber 20
24 wall of chamber 20
25 inside of chamber 20
26 outside of chamber 20

27 patient gurney
28 wheels for quick opening closure
31 defibrillator/cardiac monitor
32 suction equipment
33 regulator/ventilator
34 code cart
35 blood gas monitor
36 arterial blood pressure manometer
37 EKG monitor
38 rectal core thermistor
39 Thumper-Michigan CPR controls
41 breathing gas mixer
42 endotracheal tube connected to oxygen enriched breathing gas mixture
43 tunnel connecting main chamber to monoplace chamber
51 NIR oxygen monitor (inside chamber)
52 NIR oxygen monitor (outside chamber)
60 emergency personnel (doctors, nurses, et al.)
81 door
82 door
100 stabilized near infra-red light source
101 light source (e.g., Oriel 66195)
102 Lamp (e.g., 100 watt Oriel 6333)
103 Hot mirror housing
104 Visible light fiber optics adaptor (e.g., Oriel 77797)
105 Hot mirror (e.g., Andover 775 FW 82-50S)
106 Near infrared fiber optics adaptor (e.g., Oriel 77797)
107 fiber optics light conduit
108 Photo feedback system (e.g., Oriel 68850)
109 Power source (e.g., DC feedback Oriel 68830)
110 Stabilized power supply
111 Parabolic light collector
120 total light path
122 visible light path
124 NIR light path
200 Single point pickup unit
201 Light dam
202 Collimating lens beam probe (light input)
203 Collimating lens beam probe (background pickup)
204 Collimating lens beam probe (sample pickup-cerebral cortex)
205 Scalp
206 Skull
207 Dura
208 Pia
209 Arachnoid
210 Cerebral cortex
211 Multioptode ring pickup unit
212 NIR diffuse light path (background)
213 NIR diffuse light path (sample-cerebral cortex)
216 fiber optic cable for light input
218 fiber optic cable for background light
220 fiber optic cable for sample light
222 electric signal wire
224 computational and control equipment
226 optode frame with angular adjustment to light input and pickup
228 mirror lined or polished surface
230 Fresnel pickup unit
231 Fiber optics bundle (e.g., Dolan Jenner XL 536T)
232 Light dam assembly
233 Rubber boot
234 Fresnel lens (e.g., Edmond Scientific D43,012)
235 Collimating lense (e.g., Donan Jenner LH 1200)
236 Fresnel upper housing assembly
237 Fresnel lower housing assembly
250 spherical mirror pickup optode
251 optode barrel
252 encap housing
253 mirror housing
254 mirror cap
255 spherical mirror (such as Edmond Scientific part no. J43-544)
256 O-ring light seal
300 Dual wave interval spectrophotometer
301 Optical enclosed chopper (e.g., Oriel 75155)
302 Bifurcated fiber optics bundle (e.g., Oriel 77533)
303 Spectrograph (e.g., Oriel 77400)
304 Aperture
305 CCD Spectrophotometer
306 Optical grating (e.g., 600–1100 nm)
307 Charge coupled device (e.g., Oriel Inter Spec IV)
308 Amplifier
309 A/D converter card
310 Interface unit
311 Personal computer
312 Data storage unit (e.g., Syquest)
313 Monitor
314 Printer
315 Clock driver timer module
316 Computational equipment
400 Signal extraction processing software (with real time background removed)
402 Real time alternating background spectra (a 6 second integration time and a 4 second interval time)
403 Real time alternating sample spectra (a 6 second integration time and a 4 second interval time)
404 Averaging sub routine
405 Sav-Golay 2nd degree polynomial with 51 points subroutine
406 Fourier window (wave length interval) specified (for Hb, HbO, $H_2O$, and cytochrome oxidase)
407 DC signal removed by subtracting average absorbance from actual value
408 Fourier transform analysis subroutine
409 Fourier deconvolution analysis subroutine
410 Result stored
411 Corrections summed
412 individual noise (cosmic) pixels corrected subroutine
413 Difference absorption spectra sub routine
415 average absorbance computed (result of integral/wavelength interval)
416 signal extracting processing hardware (without real time removal)
417 first (fundamental) real component of Fourier transform
418 real time background spectra (20 each, a 6 second integration time and a 4 second interval time)
450 absorbance curve for oxygenated hemoglobin
452 absorbance curve for de-oxygenated hemoglobin
454 absorbance curve for oxidized cytochrome oxidase
456 absorbance curve for reduced cytochrome oxidase
458 absorbance curve for water
460 correction applied to cytochrome oxidase signal
469 deoxygenated hemoglobin peak at 760 nm
500 Dual wave interval spectrophotometer
510 hyperbaric resuscitation system (remote patient access)
520 monoplace hyperbaric chamber
534 external/internal IV
539 Thumper-Michigan chest compression device
560 emergency room personnel (doctors, nurses, et al. (ready to provide patient with direct access))
611 exit ring for light input
620 hyperbaric chamber (such as a conventional hyperbaric chamber)
630 Optional Fresnel lens pickup unit

DETAILED DESCRIPTION OF THE INVENTION

In FIGS. 9 and 10, the preferred embodiment of the hyperbaric resuscitation system of the present invention is designated by the numeral 10.

The system is preferably composed of a hyperbaric chamber 20 with minimum dimensions of 96" (2.44 m) in diameter with a 14' (4.27 m) usable length, capable of being pressurized to four atm abs, and built to pressure vessel human occupancy (PVHO) standards. Access to the chamber 20 can be through doors 81 and 82 large enough to roll equipment and patient 1 in and out (e.g., 34"×54"–86 cm×137 cm). Access is preferably also provided by a quick-opening closure 22 with an opening diameter equal to the diameter of the chamber 20. The entire resuscitation cart 21 will roll in and out of the chamber. The resuscitation cart comprises the patient gurney 27, floor space around the gurney 27 for two to five emergency personnel 60, a capnometer (monitor of CO2 in exhaled gas—not shown), a defibrillator/cardiac monitor 31 with intravascular pressure monitoring capability, suction equipment 32, volume cycled patient regulator/ventilator 33, American Heart Association approved code cart 34, a blood gas monitor 35, an arterial line blood pressure manometer 36, continuous EKG cardiac monitor with recorder 37, rectal core thermistor 38, x-ray equipment (not shown) for anterior/posterior neck, chest, and abdomen conventional views by portable x-ray equipment, a pulse oximeter (not shown) and a NIRoscope 51 capable of rapidly and continuously measuring cytochrome oxidase redox ratio in the cerebral cortex of the patient 1.

If one is willing to forego the quick-opening closure 22, one could use a standard hospital hyperbaric chamber commercially available from Perry Oceonographics Company.

All NIRoscope-related equipment on the resuscitation cart 21 must be checked for suitability for operation in an hyperbaric atmosphere and, if necessary, the requisite modifications must be made. AU above equipment is installed on a cart capable of being moved in and out of the entrance doors 81/82 of hyperbaric chamber 20.

Figure 11:
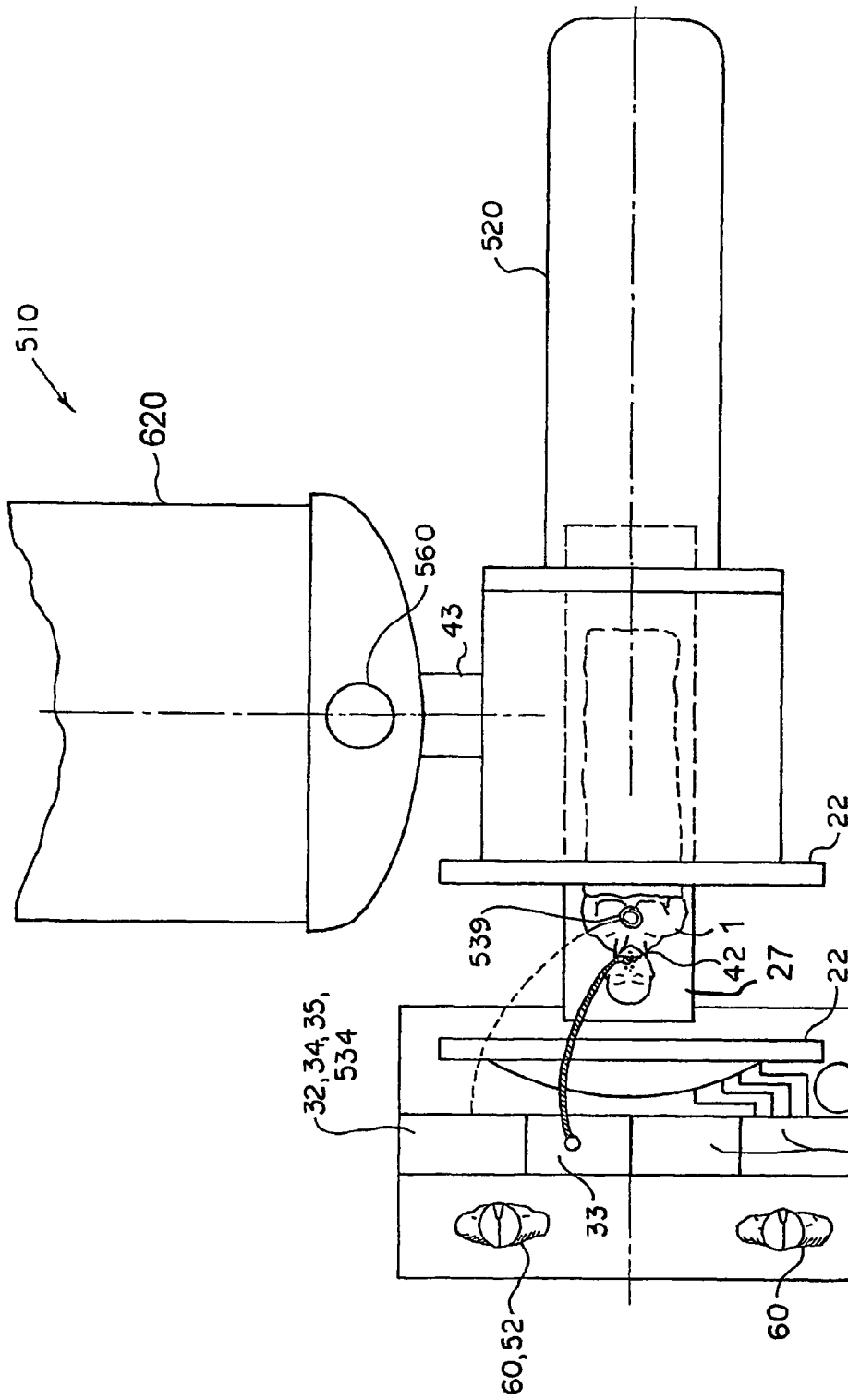
FIG. 11 is a top view of another embodiment of the apparatus of the present invention.

The method of the present invention comprises placing a patient 1 with endotracheal tube in place into hyperbaric chamber 20 having a volume sufficient to enclose a human patient and at least two operating personnel 60, pressurizing the hyperbaric chamber 20 to greater than existing barometric pressure (preferably to at least 1.5 atmospheres), providing oxygen-rich gas to be breathed by the patient 1 through endotracheal tube 42, pressurizing the oxygen-rich gas a pressure similar to that of the hyperbaric chamber 20, and monitoring oxygen in cerebral tissue of the patient 1 with a non-invasive monitoring means (such as NIRoscope 51, 52). The method preferably also includes the step of automatically regulating the concentration of oxygen in the oxygen-rich gas in response to readings of the non-invasive monitoring means. At the option of the emergency center/attending emergency physician, a monoplace chamber 520 can house the patient 1 and all ACLS procedures conducted from the outside of the chamber 520 by robotic design (see FIG. 11). Chamber 520 is provided with a connecting tunnel 43 to chamber 620 in case patient access is needed by medical personnel 560. In such a case, medical personnel 560 would enter chamber 620, chamber 620 would be pressurized to the same pressure as chamber 520, then the personnel 560 would enter chamber 520 to work with patient 1.

Description of Present Niroscope Algorithm Technology—Multi-Component Analysis (MCA)

Niroscopy is the application of absorption spectroscopy in the near infrared range for measuring the change in concentration of specific chromophores. The primary chromophores that are designated for measurement are oxidized and reduced cytochrome oxidase and oxygenated and deoxygenated hemoglobin.

Currently, measuring the change of the concentration of these chromophores by niroscopy is based on the following considerations and procedures. Given an absorption curve over a range of wave lengths in the near infrared region (700–950 nm) and assuming Beer's law is applicable, a set of simultaneous equations can be generated which, when solved, will result in concrete values for the relative concentrations of each of the chromophores. The number of equations is equal to the number of chromophores whose concentrations are to be determined. For example, in the brain, for the near infrared spectral region, there are the four aforementioned chromophores. If any four different near infrared wave lengths are selected for making total absorption measurements, four total absorption values will be obtained. Using Beer's law, it is possible to solve for the concentration of each of the chromophores. The equations that are generated will contain the following variables: total absorption, chromophore extinction coefficients, concentration of each chromophore, and path length. Total absorption is obtained by direct measurement. Chromophore extinction coefficients are determined experimentally. Total path length involves a complex series of events which may be considered constant for the system and therefore can be assumed to be unity. By solving these simultaneous equations by matrix operations it is possible to calculate the relative concentrations of each of the chromophores. The ratio of oxidized and reduced cytochrome is then calculated from the values obtained from the solution of the equations.

The present method has certain errors inherent in its application. These are:

1. The method assumes Beer's law is linear. However, Beer's law is not linear in a scattered media or in the presence of large absorbance changes of other chromophores.
2. The extinction coefficients of cytochrome have been measured in bloodless rats where cytochrome oxidase was assumed to exist either entirely in the oxidized or completely reduced state. Experimental evidence has shown that a condition of total oxidation or reduction of cytochrome oxidase does not exist. Also a slight hemoglobin contamination was present during these measurements for which no correction was made. Therefore, the relative concentrations of the cytochromes that were calculated were not accurate.
3. The effects of water absorption overtones cannot be taken into account by modeling with Beer's law.
4. Because of the limitations associated with items 1 and 2, current niroscopic techniques do not permit consistent measurements in adult humans. The signal obtained in adult humans is extremely faint since it is being masked by the high hemoglobin concentration.

The present inventors perceived a need to develop niroscopic techniques that would obviate these limitations. The following is the theoretical description of the bases of the innovation of the present invention.

It is the contention of the present inventors that the aforementioned limitations of the niroscopic techniques can be overcome by the use of a specific range of near infrared waves (600–1100 nm) from which the change of a single absorption curve is obtained and used directly or corrected and from which the relevant data can be extracted via model-free mathematical operations, i.e. Fourier transform/deconvolution analyses (FTA/FDA). Fourier transforms are commonly used for infrared analysis and in digital signal filtering techniques, but are not so used in analyses of near infrared data. There is no obvious theoretical reason why such analyses could not be performed on data obtained from near infrared analyses. Therefore, the present inventors decided to incorporate such analyses in theoretical models.

The data used to demonstrate our proposed Fourier transform operations are derived from a theoretical construct. A family of spectra is generated using Beer's law, and a set of measured extinction coefficients for each of the chromophores (Nioka 1991), and assuming a certain published physiological concentration of each chromophore obtained from Cope (1988) and Miyake (1991). After assuming hemoglobin is 100% oxygenated, each calculated spectrum for a specific cytochrome oxidase (cyt-aa$_3$) redox ratio (i.e. varying from reduced to oxidized in steps of 10% is plotted as optical density versus the wave length range of 700 to 950 nm (FIG. 1)).

Figure 2:
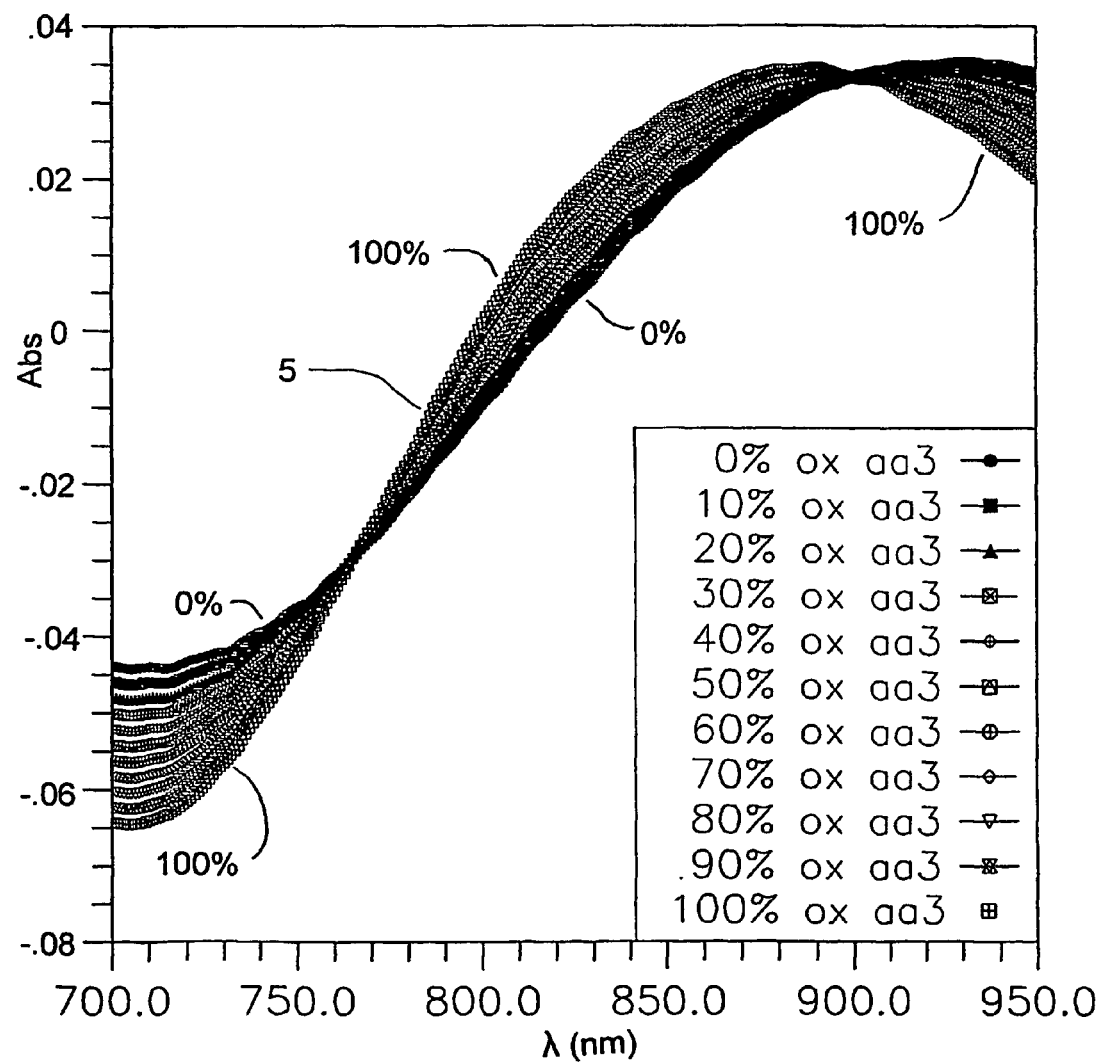
FIG. 2 shows the same absorption curves of FIG. 1, with D.C. component removed by subtracting the average absorption value of the spectrum at each wave length from the original spectrum.
Figure 3:
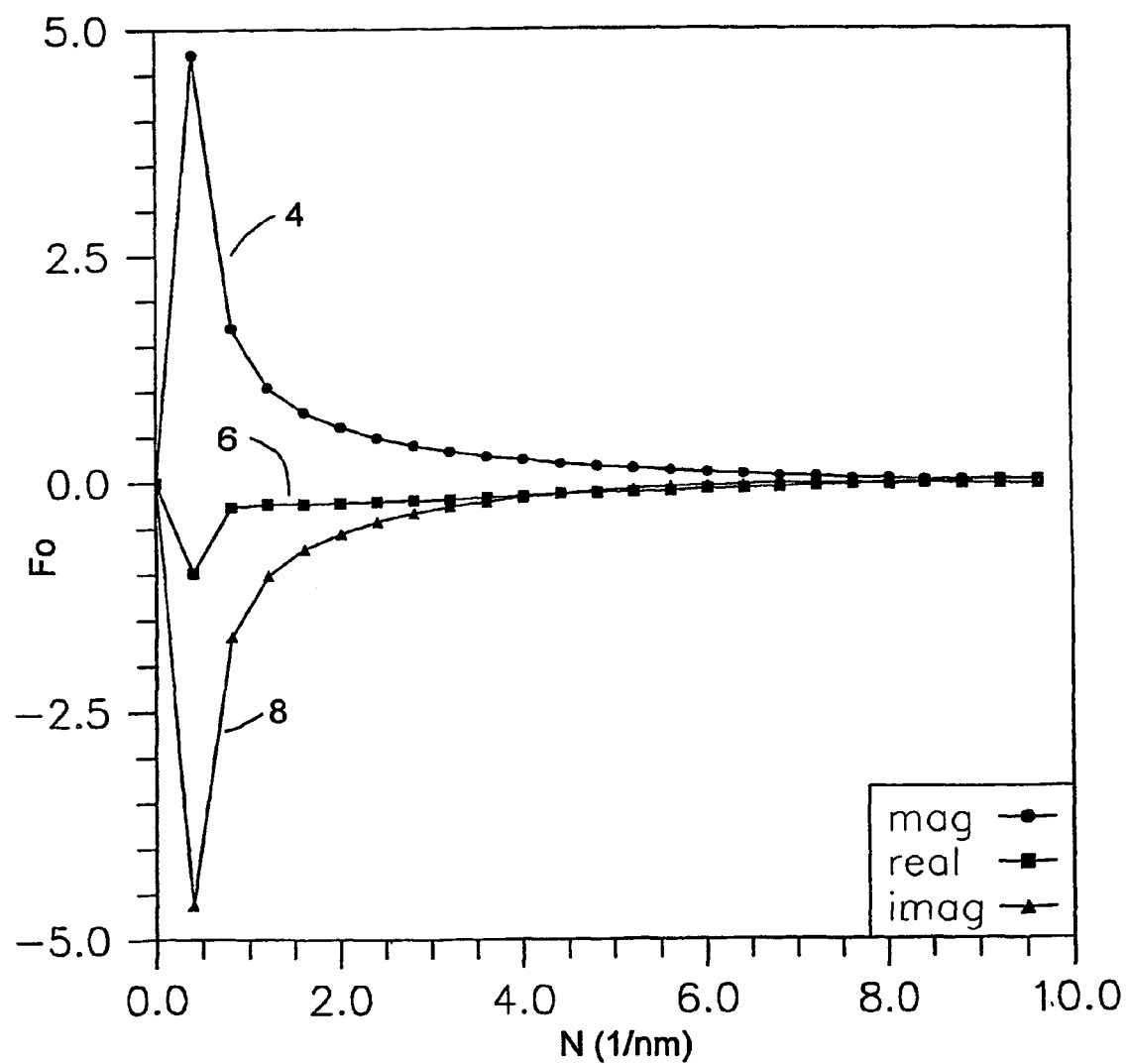
FIGS. 3, 4, and 5 are Fourier transforms of absorbance curves.
Figure 4:
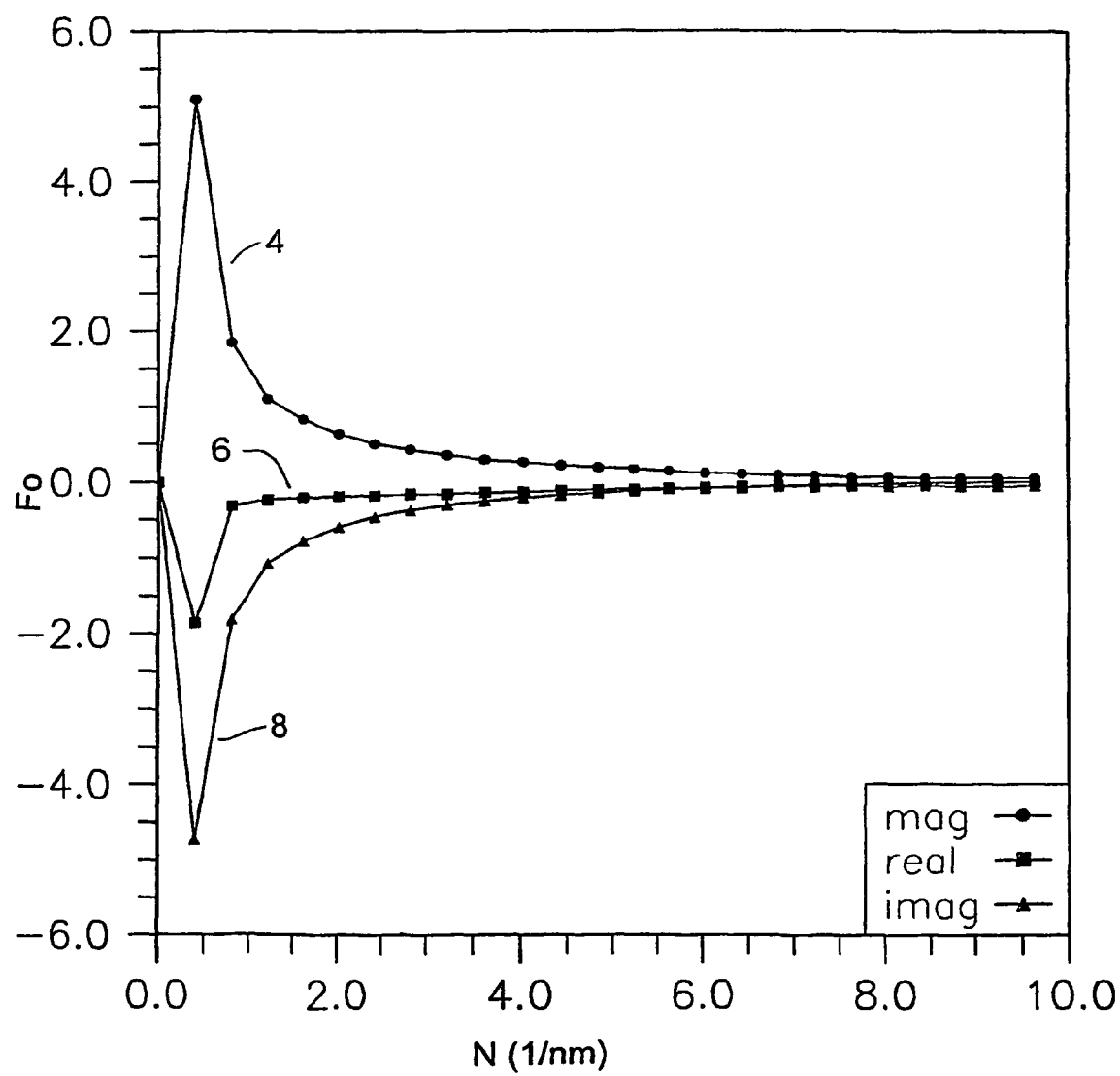

The cyt-aa$_3$ absorbance extraction is as follows. Each spectrum in the resultant family of spectra (FIG. 1) is subjected to removal of the DC component by subtraction of the average (i.e. total area under each curve divided by the wave length interval), resulting in the curves shown in FIG. 3. The curves in FIG. 3 are then subjected to Fourier transform procedures. Form the results of Fourier transforms, it is observed that the only value that changes as a function of the cytochrome redox ratio is the real component in the fundamental frequency. FIG. 2 shows the amplitude of this real component of the fundamental frequency is linearly proportional to the percent oxidized cytochrome oxidase (i.e. redox ratio) to the fifth significant figure (i.e. 0.04212 div./redox ratio of cyt-aa$_3$).

Figure 25:
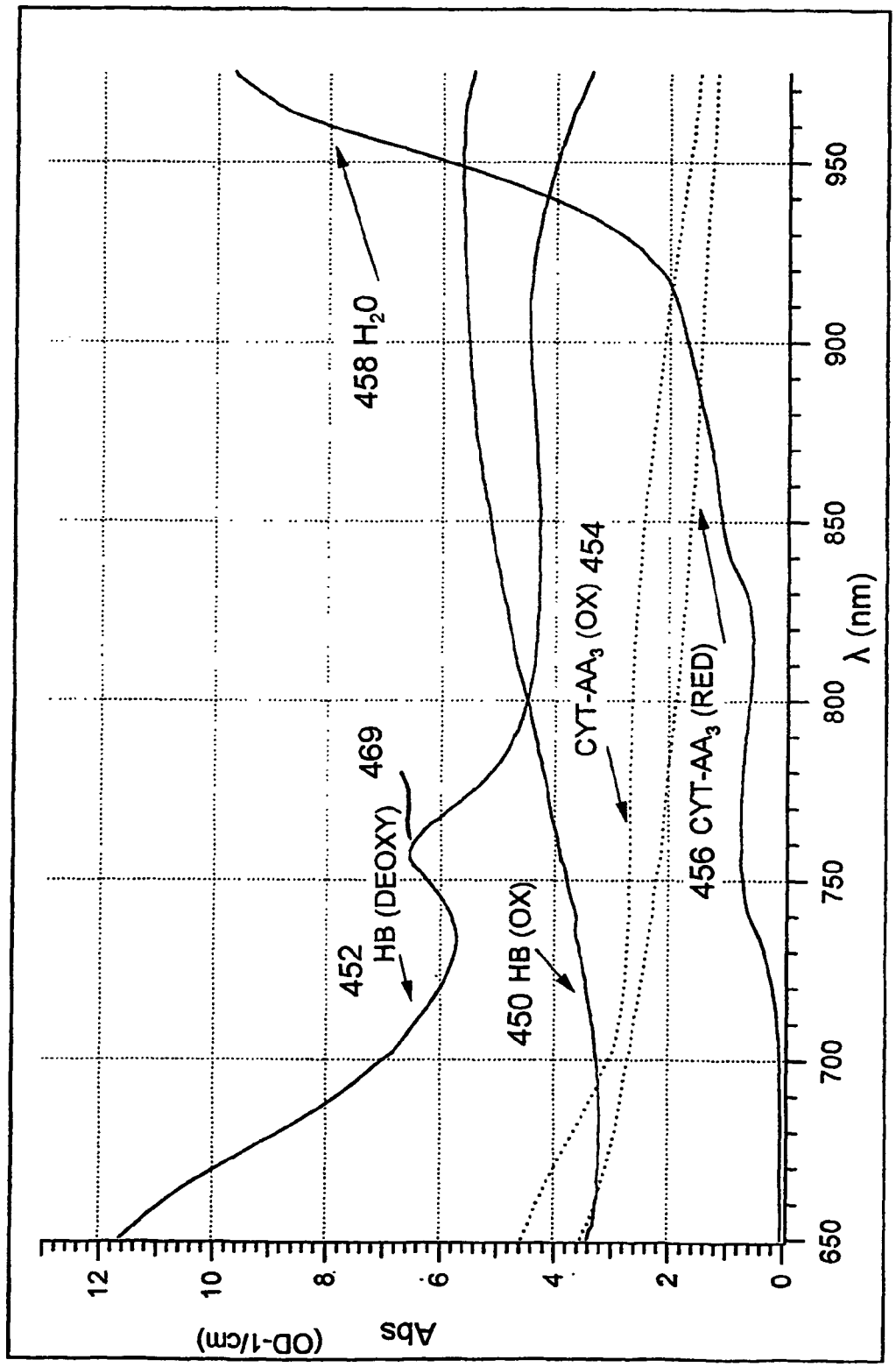
FIG. 25 shows absorption curves for hemoglobin, water and cytochrome oxidase.

The theory of Fourier transforms (Brighan 1988) explains the reason for linearity. FIG. 25 displays the absorbance for each chromophore in the 700–1100 nm wave length range. Notice that the oxidized cyt-aa$_3$ spectrum 454 completes one cycle (i.e. the fundamental frequency in the 700–950 nm wave length interval). None of the other chromophores have this feature. Fourier transform operator separates out the contribution of each component harmonic. The only spectrum completing one cycle in the chosen wave length interval is oxidized cyt-aa$_3$. The effect is to extract the cyt-aa$_3$ while filtering out all other absorbance bands. Signal extraction is improved by another Fourier transform feature. When a Fourier transform is performed on a function (i.e. absorbance spectra), one real value and one imaginary value will be determined for each component frequency. The real value represents the symmetrical portion of the component frequency, and the imaginary represents the asymmetrical portion of the component frequency. For a wave length interval of 700–950 nm, cyt-aa$_3$ is symmetrical (i.e. only the real component is representative) which once again extracts the cyt-aa$_3$ absorbance peak and filters out all others. This is the reason why the real component of the fundamental frequency is significantly linearly proportional to cyt-aa$_3$ redox ratio.

The extraction technique is also quite robust with respect to signal to noise ratios (S/N). Calculations have shown, when reducing the S/N ratios from 45 to 1.39, the fundamental real component 468 does not change appreciably (±2%). Even when considering inexpensive, noisy spectrophotometers which have a low S/N ratio, the S/N, although low, usually remains relatively constant. It will be removed with the DC portion of absorbance spectra. This implies that as long as the signal can be extracted (i.e. not completely buried) noise will have little effect. Removing the DC component and the Fourier transform also reduces the effect of noise due to scattering.

The effects of large variations in Hb and water were studied by generating another theoretical construct of spectra (i.e., high and low concentrations for Hb and water). These spectra were processed, and the resultant real component of Fourier transfer change approximately 2%. Because our goal is to have Hb or water affect the signal by 1% or less, a second Fourier transfer tool may be required.

This second tool, Fourier deconvolution analysis (FDA) has been explained in detail by Blass (1981). The expected NIR total absorbance spectra is a combination of the major absorbance curves shown in FIG. 25. Both de-oxygenated Hb 452 and reduced cytochrome oxidase 456 have spectra resembling exponential decay, except de-oxygenated Hb has a narrow peak 469 with a half width of 30 nm, centered at approximately 760 nm. The oxygenated form of hemoglobin 450 and the oxidized state of cytochrome oxidase 454 have broad peaks, with cytochrome oxidase having a half width of 175 nm (725–900 nm) centered at 830 nm and deoxygenated hemoglobin having a halfwidth of 400 nm centered at 812 nm. Because both water and de-oxygenated Hb have distinct peaks, Fourier self-deconvolution can be applied (Blass 1981). It is a method for resolving intrinsically overlapping absorbency bands (an NIR total absorbance spectrum) into each component absorption curve of interest (de-oxygenated hemoglobin and water). It is, however, noise sensitive (i.e., will resolve noise if S/N ratios are large enough) and therefor requires an expensive (noise free) CCD spectrophotometer. If a noise free (i.e., S/N greater than 1000) spectrophotometer is used, FDA allows monitoring deoxygenated hemoglobin, and water separately. If there is a change in cyt-aa$_3$ absorbance inflicted by Hb or water overtones, a corresponding correction can be made to the cyt-aa$_3$ result. The ability to monitor cerebral edema or de-hydration (changing water content) will also be useful information and could be easily displayed separately.

Figure 13:
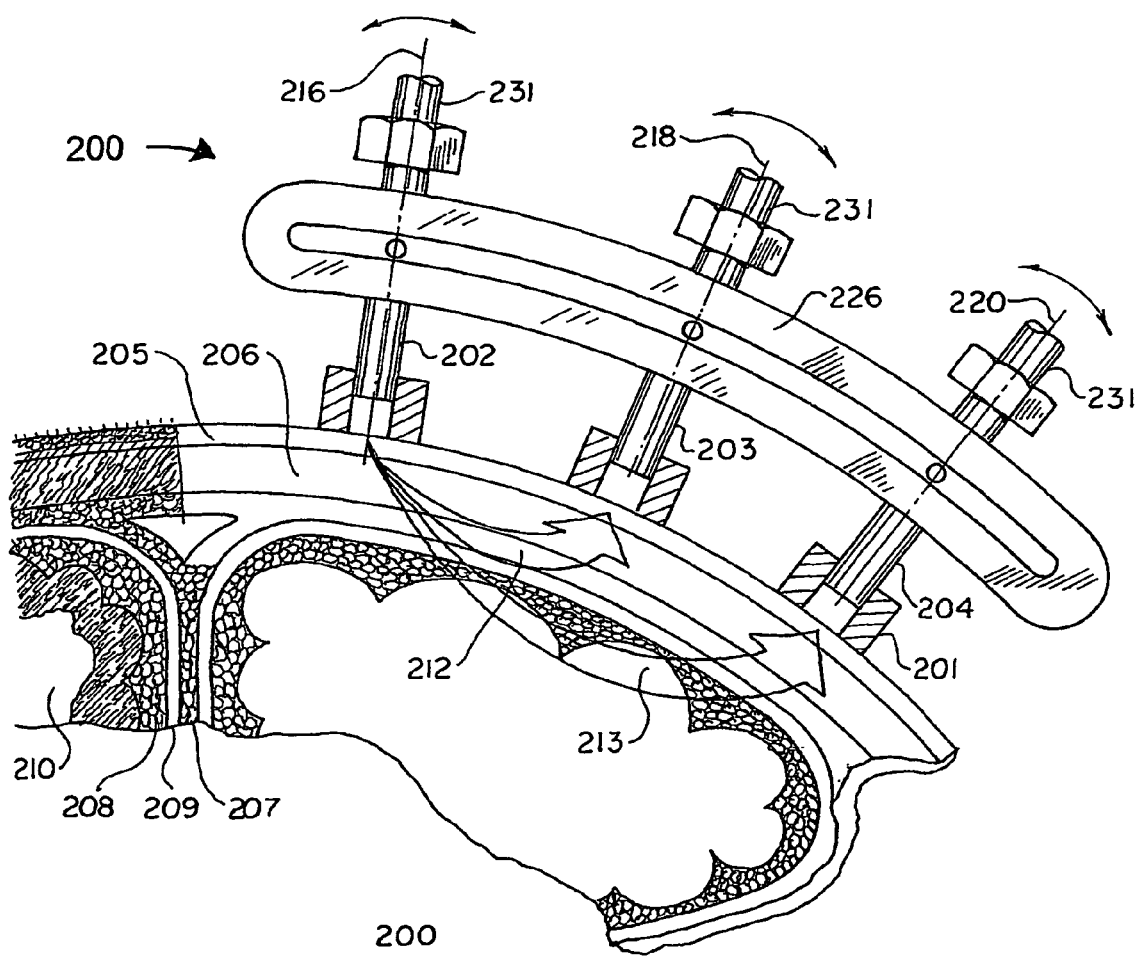
FIG. 13 is a schematic view of a single point pickup unit.
Figure 14:
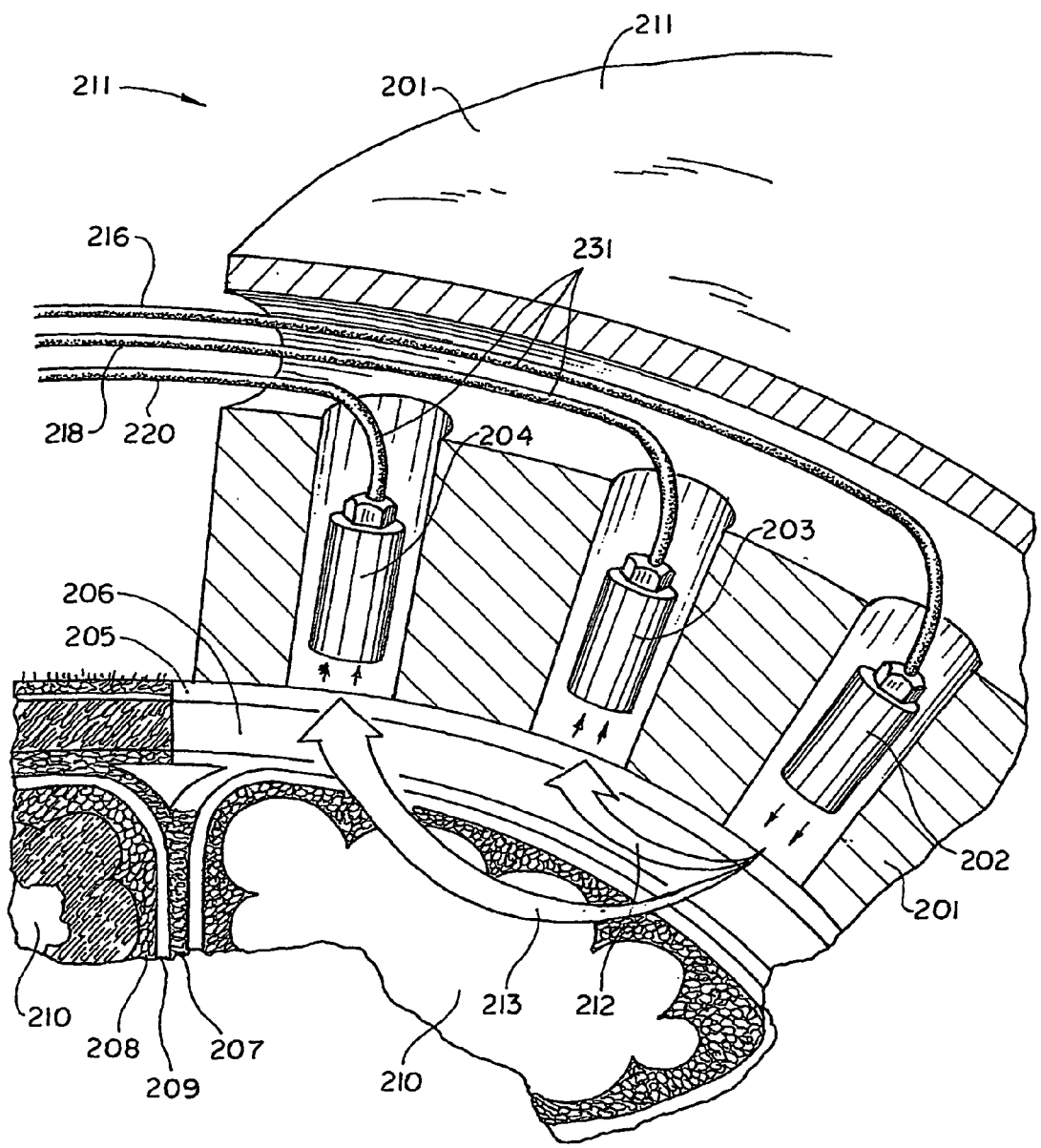
FIG. 14 is an illustrative view of a ring pickup unit (to optimize light collection).
Figure 15:
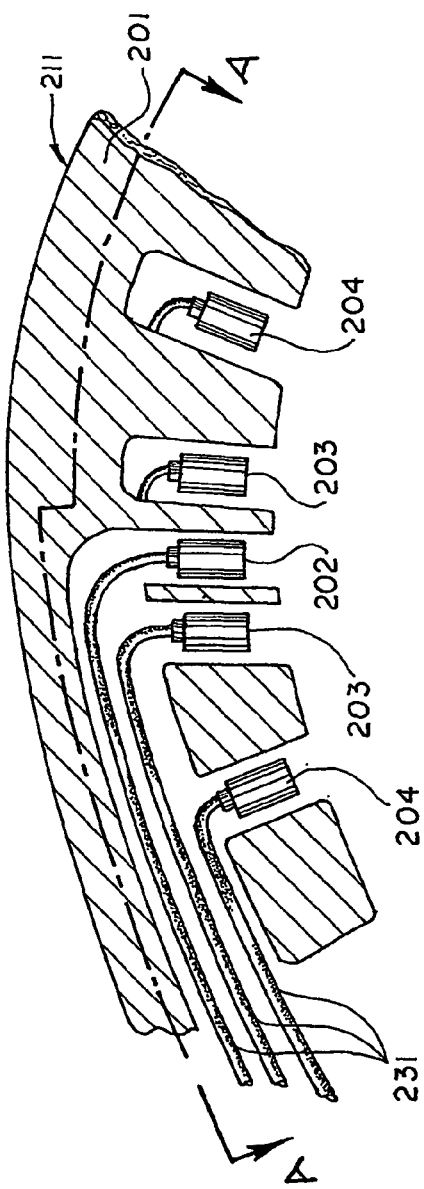
FIG. 15 is schematic view of a ring pickup unit.

A third tool called differential absorption spectroscopy may also be utilized to enhance the extraction of the cyt-aa$_3$ absorbance contribution. Rather than use an arbitrary reference (water for transparent spectroscopy or water plus microspheres for diffuse spectroscopy) a reference spectra is taken in vivo either at a certain time (admission of the patient) or tissue location (lower distance from light source than sample—see FIGS. 13, 14, or 15, probe 203). Using these spectra as reference will allow sensitivity to be increased by measuring change in absorbance rather than the actual value of absorbance.

In summary, increasing the sensitivity of measurement with differential absorption spectroscopy and by combining the accurate measurement of FTA with the possible correction to the cyt-aa$_3$ measurement made by FDA, we can non-invasively measure the change in the cyt-aa$_3$ redox ratio with a model-free analysis using standard digital signal conditioning techniques. This should result in improved accuracy in adolescent swine and ultimately in the adult human head.

Data Handling Requirements

Figure 5:
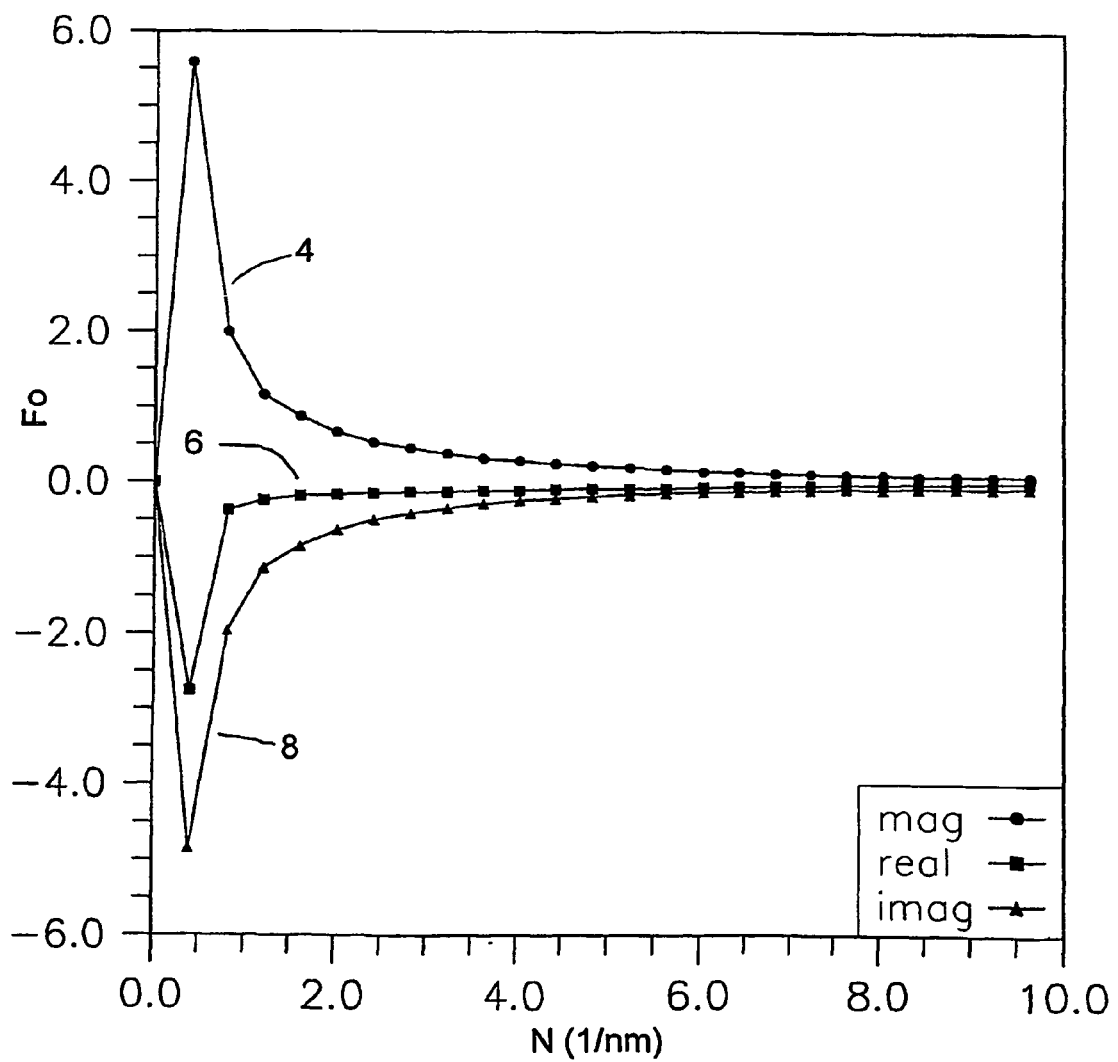
Figure 6:
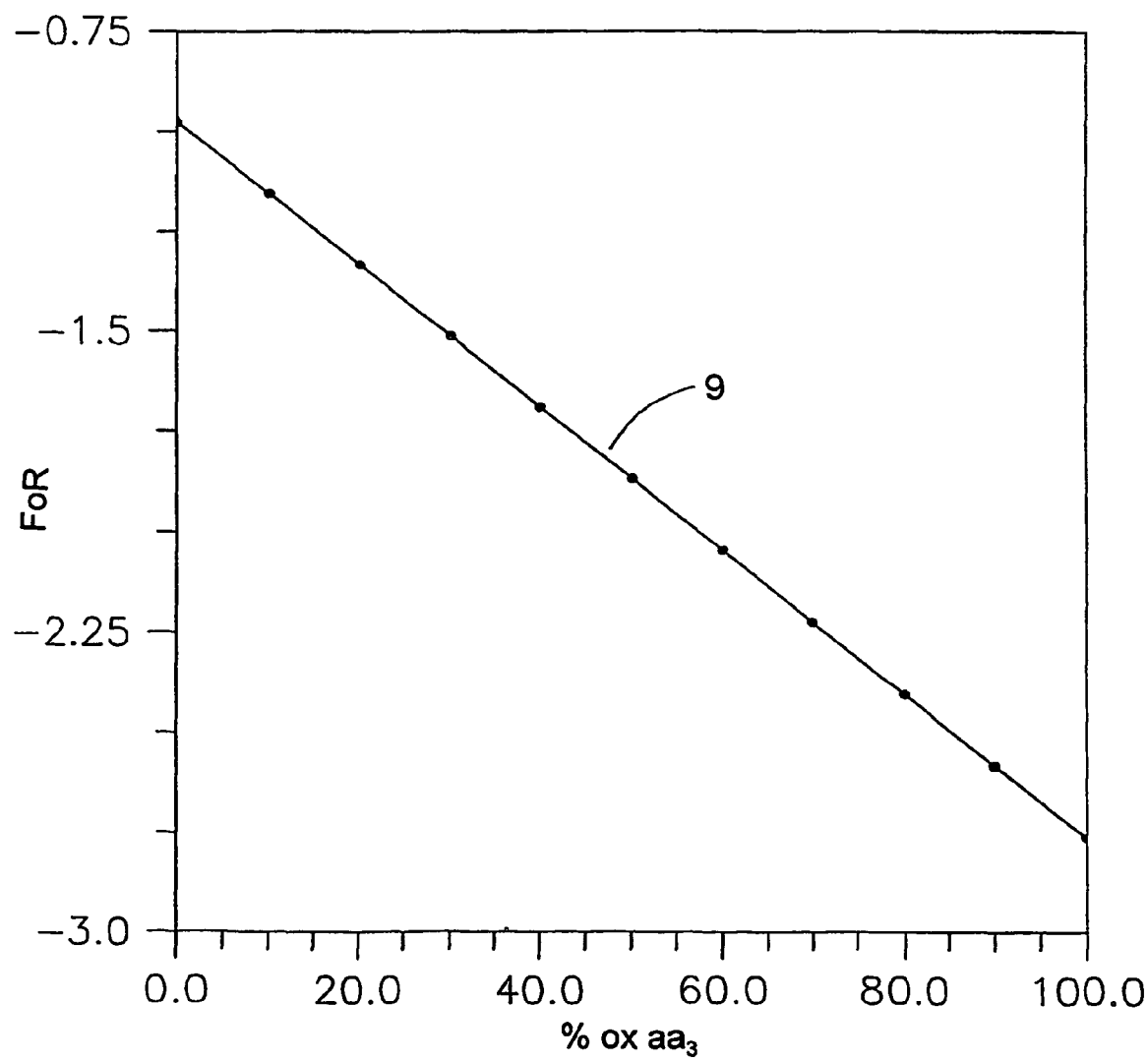
FIG. 6 is a plot of the magnitude of the first real component of the Fourier transform (axis of abscissa) versus percent oxidized cytochrome (axis of ordinate). It was found to be linear to the fifth significant figure (i.e., in this case −0.017865) and therefore expected to be an extremely sensitive indicator of oxidized cytochrome oxidase.

The preferred equipment (see FIG. 5) comprises a near infra-red light source 100, an optical pickup unit 211, and dual wave interval spectrophotometer 300, and computational equipment 316.

Figure 12:
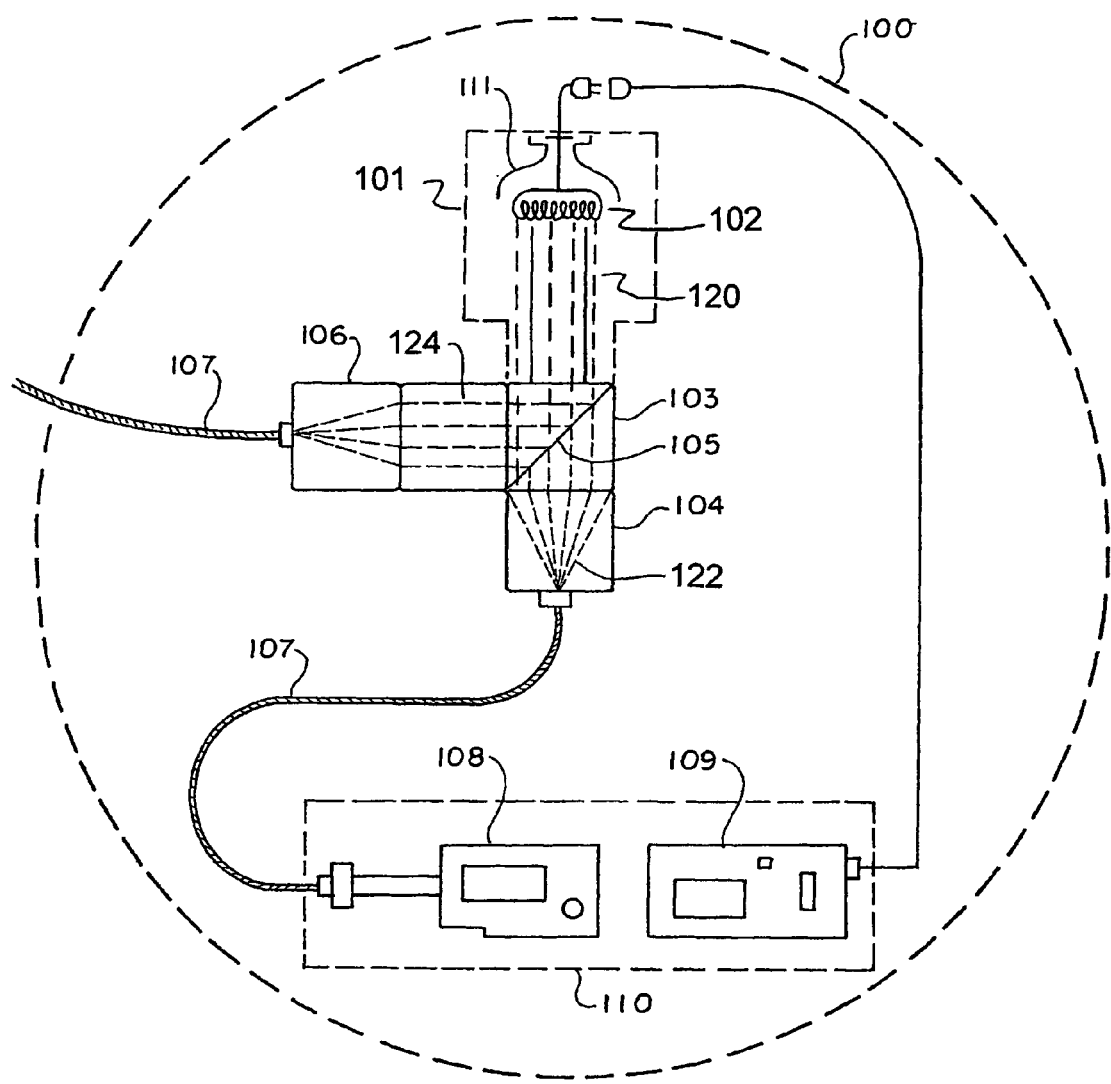
FIG. 12 shows the NIR light source of the present invention.

Near infra-red light source 100 (see FIG. 12) is preferably a 100 watt power light source 101 in a steady or pulsating mode (frequency range 0.5–2 Hz). An example of a suitable unit would be Oriel 100 watt quartz halogen light source with DC stabilized radiometric power supply, including photofeedback system, water filter, multiple filter holder/fiber optic adaptor (Oriel model numbers 66195, 68850, 61940, 62020 and 77797).

Figure 8:
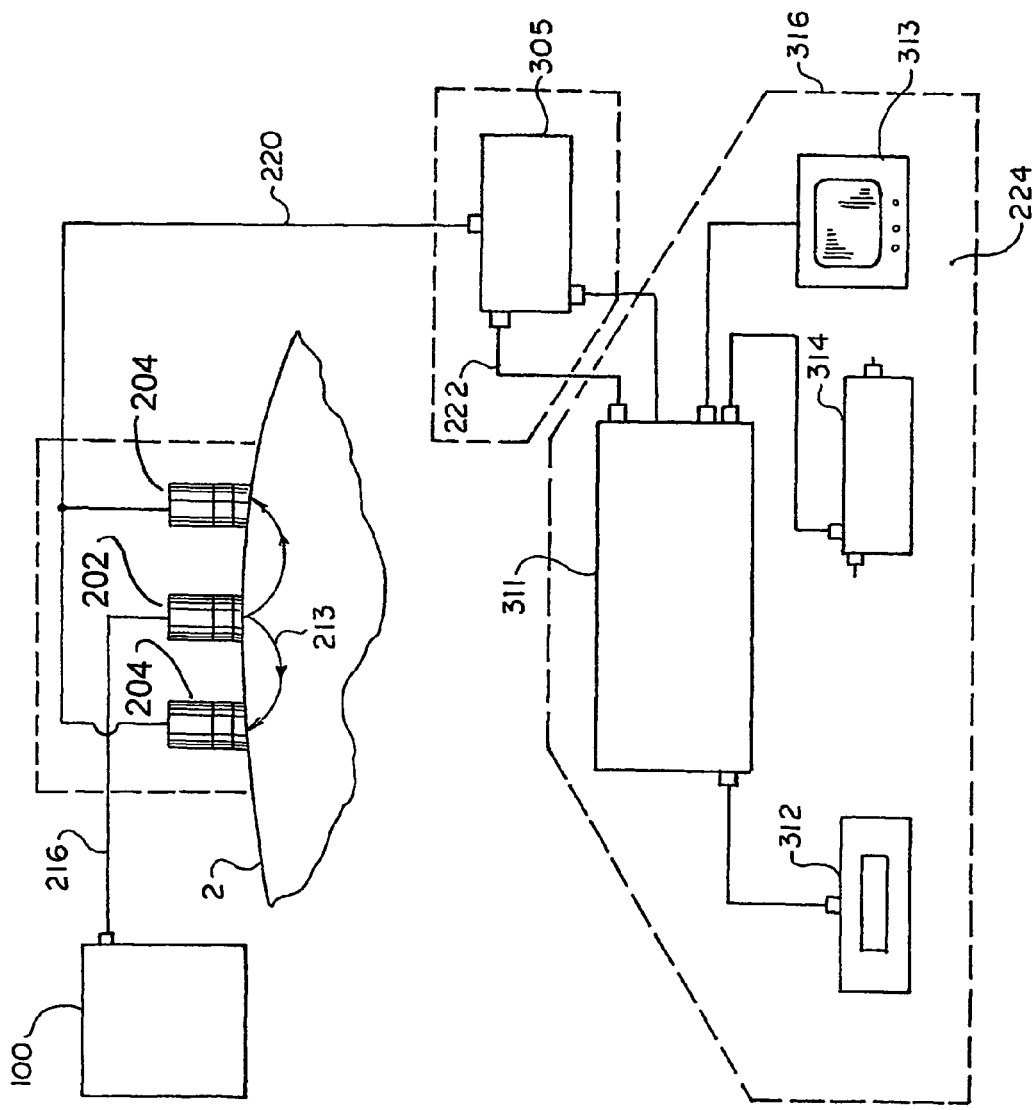
FIG. 8 is a schematic diagram of the NIRoscope without the background signal pickup optode. The background signal is taken as reference before the sample signal is taken.
Figure 16:
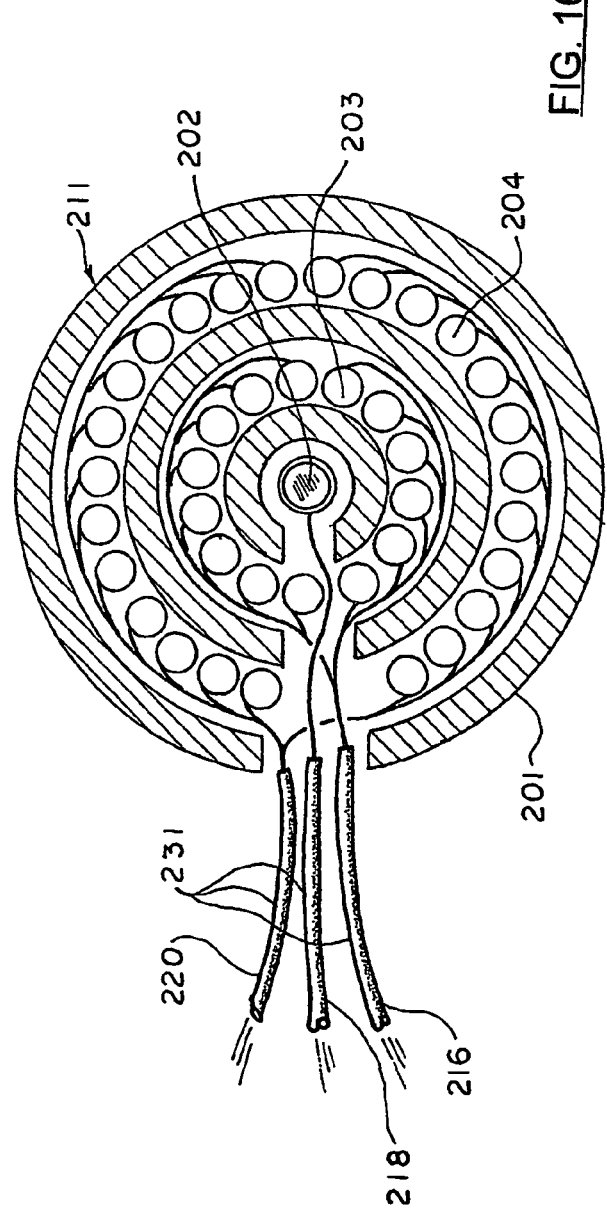
FIG. 16 is sectional schematic view of a ring pickup unit.

Optical pickup unit 200/211 (see FIGS. 13, 14, 15, 17, 18, 19) consists of fiber optics light conduit 23 connected to a single or ring of collimating beam probes 202 which inputs the light. The background light receivers are recessed single or ring collimated beam probes 203 adjusted at the proper angle to received background light. The sample light is again a recessed single collimated beam probe 202 either at the center of the rings (FIGS. 15 and 16) or in single operation adjusted at the proper angle to receive light input (FIG. 13) (Oriel model 77545 and 77645). It should be noted that if the signal separation is satisfactorily accurate, subtraction of the background signal will not be necessary thereby eliminating the need for 16 each background pickup optodes 203, optical chopper 301, and bifurcated fiber optics bundle 302. The preferred alternate equipment schematic is shown in FIG. 8.

Dual wave interval spectrophotometer 300 consists of an optical chopper 301, bifurcated bundle 302, and CCD spectrophotometer with sensitivity adequate to measure 0.005 O.D. absorbance and a dynamic range capable of measuring 4 O.D. in a wave length range of 600–1150 nm. An example of a suitable unit would be ORIEL INSTA IV CCD SYSTEM 1024×128 with instaspec wedge flange, multispec spectrograph and grating assembly (Oriel model numbers 77118, 77439, 77400, 77415).

Computational equipment preferably comprises a computer 311 with at least the speed and storage capability of an IBM personal computer, Pentium with math co-processor, 10 gigabyte hard disk with tape back up drive, a National Instruments A/D converter card, LabView software for control, and Galatic Grams 32/Igor software for analysis. All data storage will preferably be done on a 105 megabyte removable cartridge type hard disk 312 (i.e. Sydos).

The present inventors have access to a pre-existing swine model for acute resuscitation under hyperbaric oxygen conditions using external cardiac massage. Measured parameters include EKG; EEG; arterial, mixed venous, and sagittal sinus blood gases; arterial, pulmonary arterial, pulmonary arterial wedge, mixed venous, and sagittal sinus pressures; mixed venous and sagittal sinus hemoglobin saturation by direct oximetry; cardiac output; core temperature; and expired gas. Presently, the animal is maintained for two hours after resuscitation during which time normal pressures and blood gases are maintained.

The model will require modification to include validation by NIRoscope measurements against cerebral $PO_2$ measurements taken by inserting an oxygen sensing electrode through a burr hole drilled in the skull. The model should also be extended to include a 72 hour chronic model.

Outcome indicators include:
1. Documentation of time of return of spontaneous circulation;
2. Normalization of arterial blood gases (ABG's);
3. Normalization of niroscopically determined cranial tissue $PO_2$;
4. Serial improvement in single photon emission computerized tomography (SPECT) brain scan by Ceretec® (technetium hexamethylpropyleneamine oxine (HM-PAO)). Case work on injured and resuscitated divers indicates that Ceretec SPECT brain scanning elucidates perfusion/metabolism defects in the brain. (19);
5. Neurological function will be assessed using Canine Deficit Score.

To test the system and method of the present inventions, the following human studies will be conducted with proper informed consent from immediate family or custodial person with power of attorney.

Two groups of 20 human patients arriving in cardiopulmonary arrest at emergency departments with ongoing cardiopulmonary resuscitation and ACLS will be stabilized by an emergency department hyperbaric ACLS team. The patients will be randomized into two groups. Both groups will have the advantage of having hyperbaric environment modified Michigan Instrument automatic Thumper® and conventional ACLS pharmacology and ACLS algorithmic American Heart Association protocol. The subjects will be connected to a hyperbarically adapted volume cycled ventilator (10 mg/Kg for tidal volume) by endotracheal tube. Partial arterial pressure of carbon dioxide ($PaCO_2$) will be maintained at 40 mm Hg by the rate of ventilation. The control group will be brought to pressure of 4 fsw (1.22 msw—meters of sea water) and administered 100% $O_2$ by the endotracheal tube. The niroscope will record the cerebral cortex redox ratio of cytochrome $aa_3$. The treatment group will be initially administered 100% $O_2$, pressurized to minimum depths 60 fsw (18.3 msw). Once at 60 fsw (18.3 msw), both breathing gas mixture and chamber pressure will be controlled by the attending emergency physician using the output of the NIRoscope as a guide. Both groups will have cardiac monitoring by EKG and arterial continuous manometry by chart recorder. The patients post resuscitation, if successful, would have SPECT brain scan by Ceretec® HMPAO utilizing a dedicated Siemens triple head high resolution radionuclide camera with three-dimensional computer reconstructed brain images to determine the extent of ischemia-induced brain damage and the presence of potentially recoverable brain tissue. Post-resuscitation treatment will include HBOT at 1.5 ATA (atmospheres absolute) twice a day for three days and once a day for four days. Outcome indicators will include numbers 1 through 4 used in the animal experiment above, as well as percentage of improvement in HBOT resuscitated patients. In addition, neurological function will be evaluated by a to-be-determined method.

The development of superior mathematical separation techniques was necessary because although the technology for small animals and neonates has been available, it has not successfully been applied to adults.

The NIRoscope is considered necessary for HBOT resuscitation. It would also be considered an invaluable tool for routine ACLS resuscitations at one atmosphere. Niroscopy will help to optimize treatments thereby limiting the exposure of patients and attending medical personnel to pressure environments greater than that which is necessary. Thus, it helps prevent patients from being exposed unnecessarily to too high pressures of oxygen while simultaneously helping to reduce the possibility of dysbaric incidents in the attending personnel. Any technology that informs physicians as to the efficacy of their resuscitation efforts would be extremely helpful. Three different authors are proposing to use tissue or blood oxygen content for helping to evaluate success of resuscitative efforts by physicians.

Figure 17:
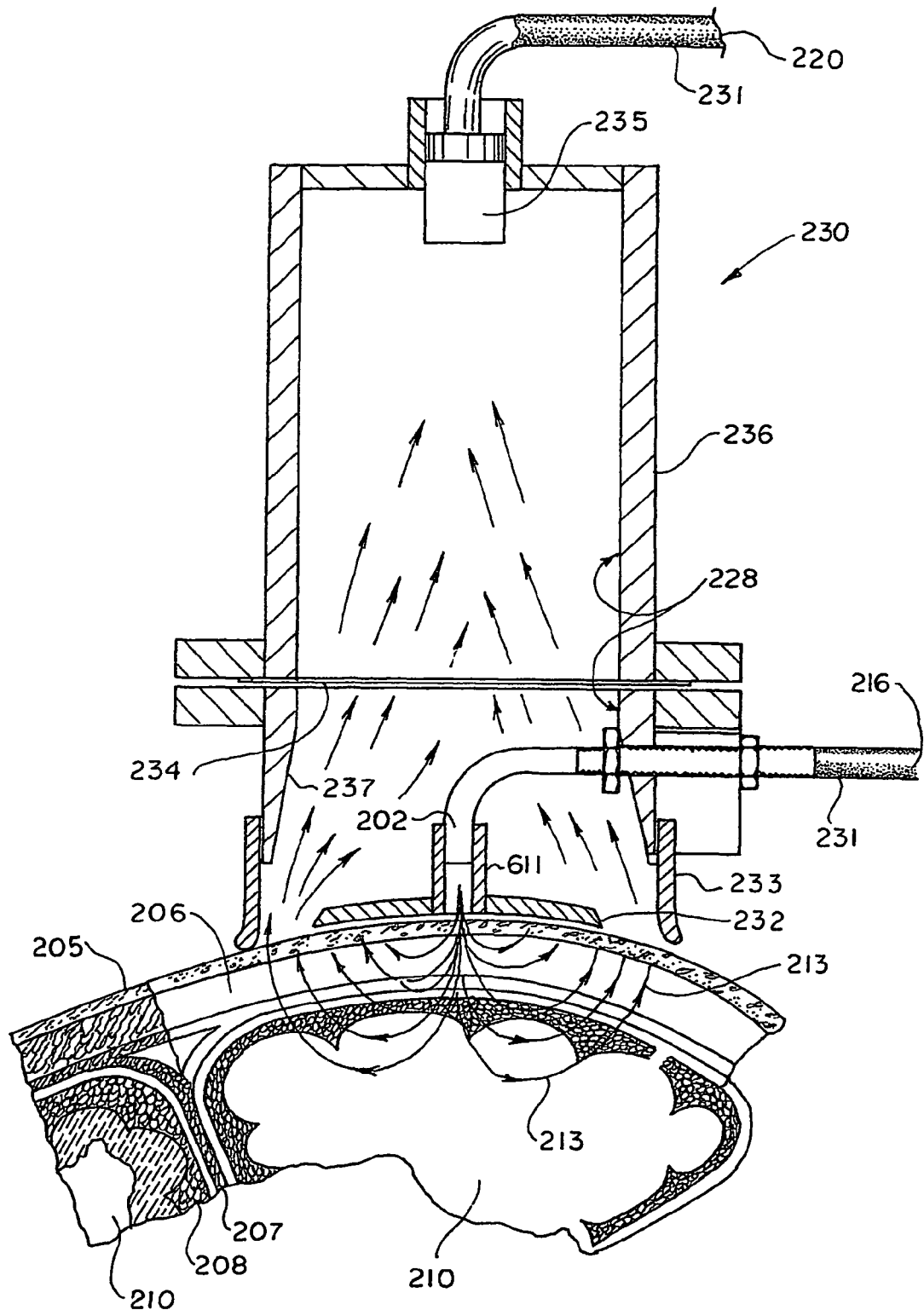
FIG. 17 is a schematic view of a Fresnel lens pickup unit with internal light input.
Figure 18:
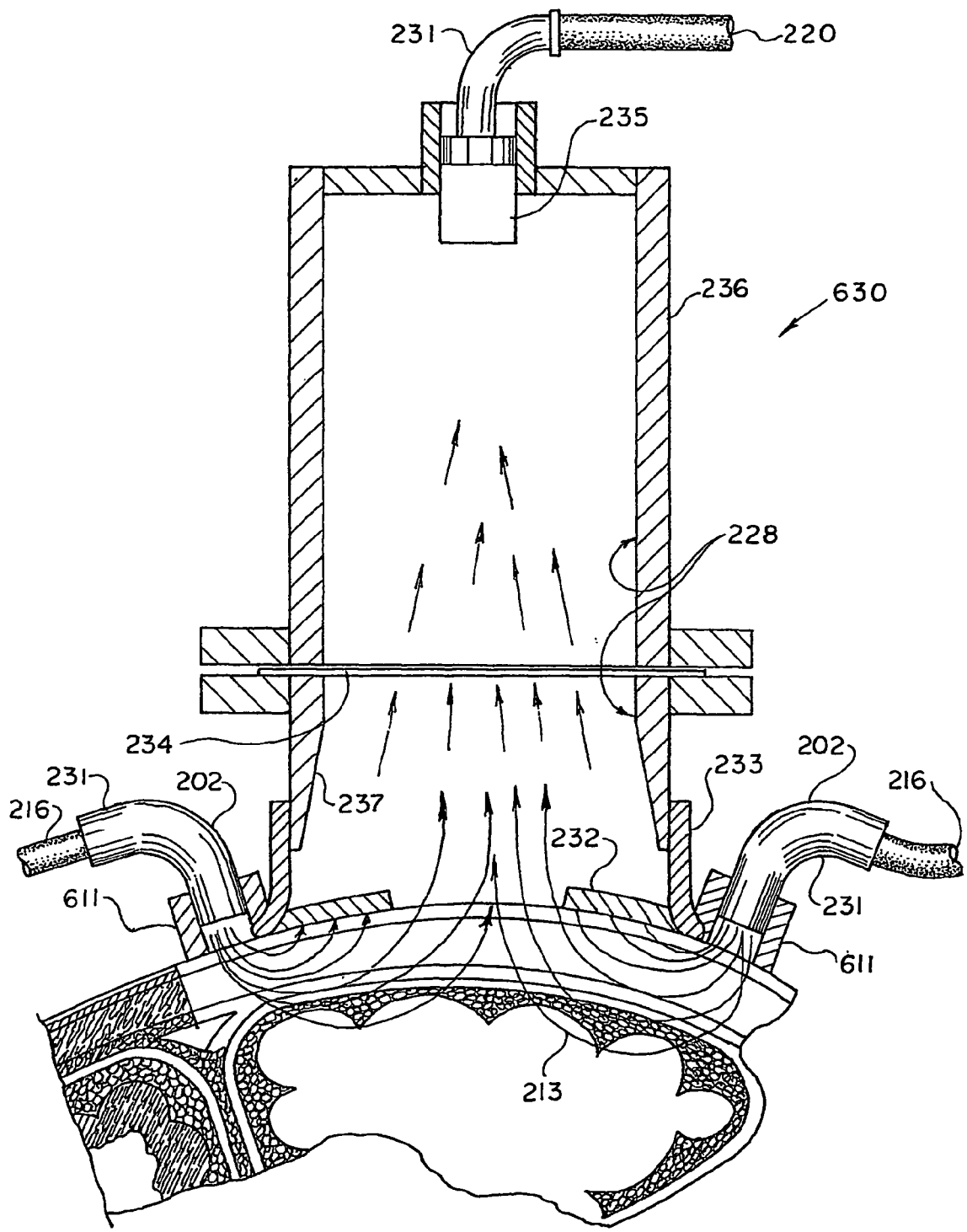
FIG. 18 is a schematic view of an optical arrangement of Fresnel lens pickup unit with external light input.
Figure 19:
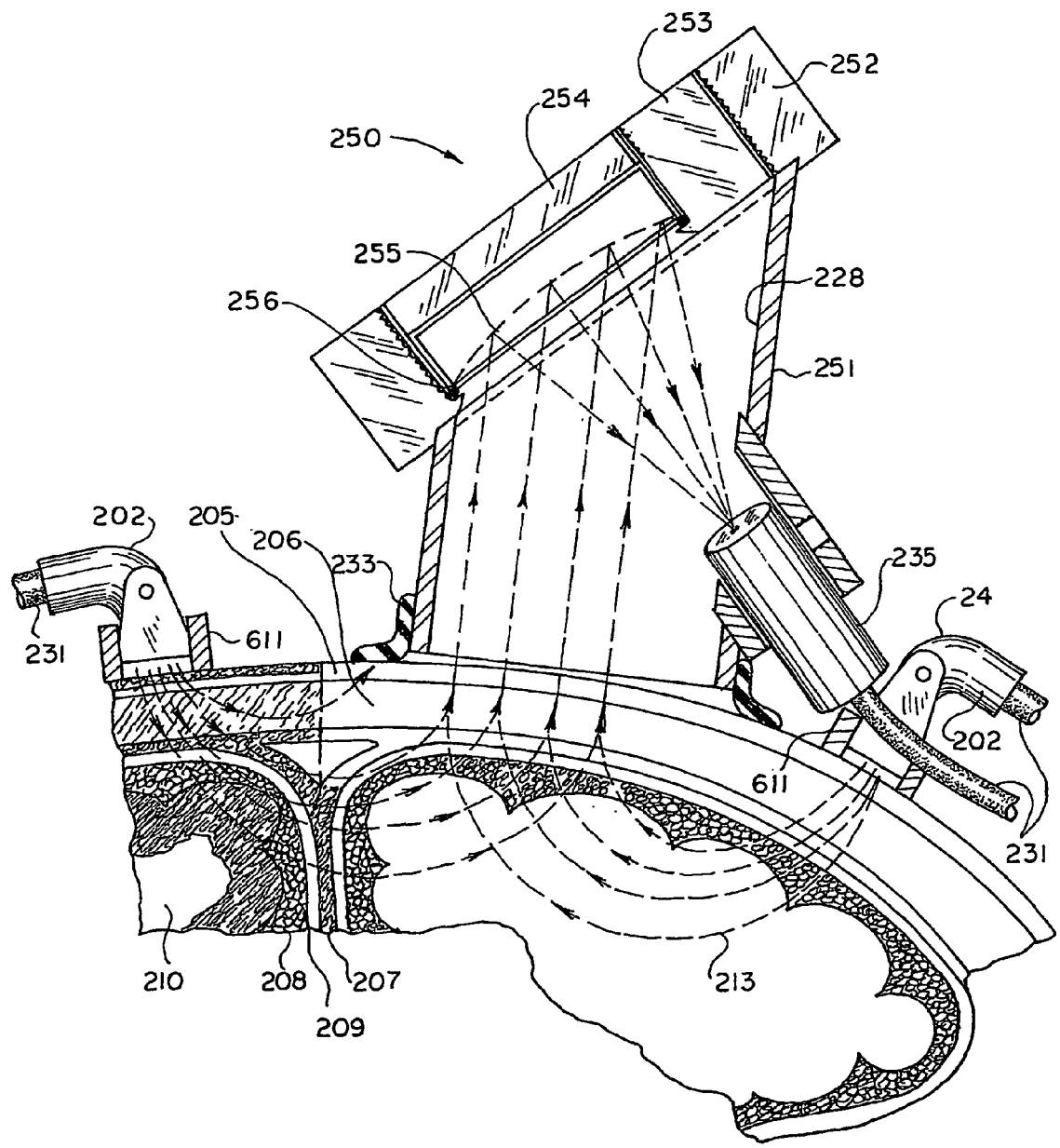
FIG. 19 is a schematic view of an optical arrangement of a spherical mirror pickup unit with external light input.
Figure 20:
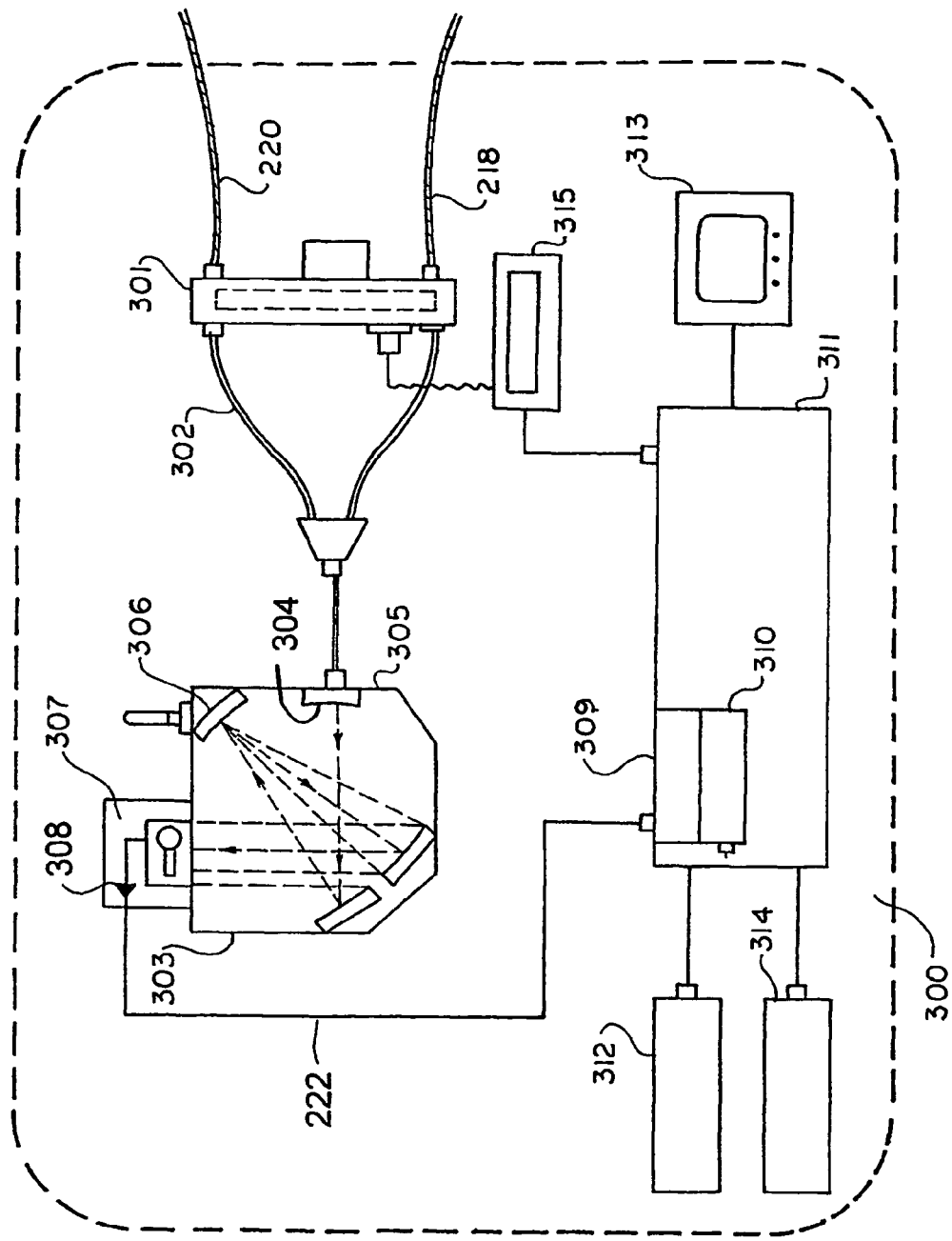
FIG. 20 shows a dual wavelength interval spectrophotometer.
Figure 21:
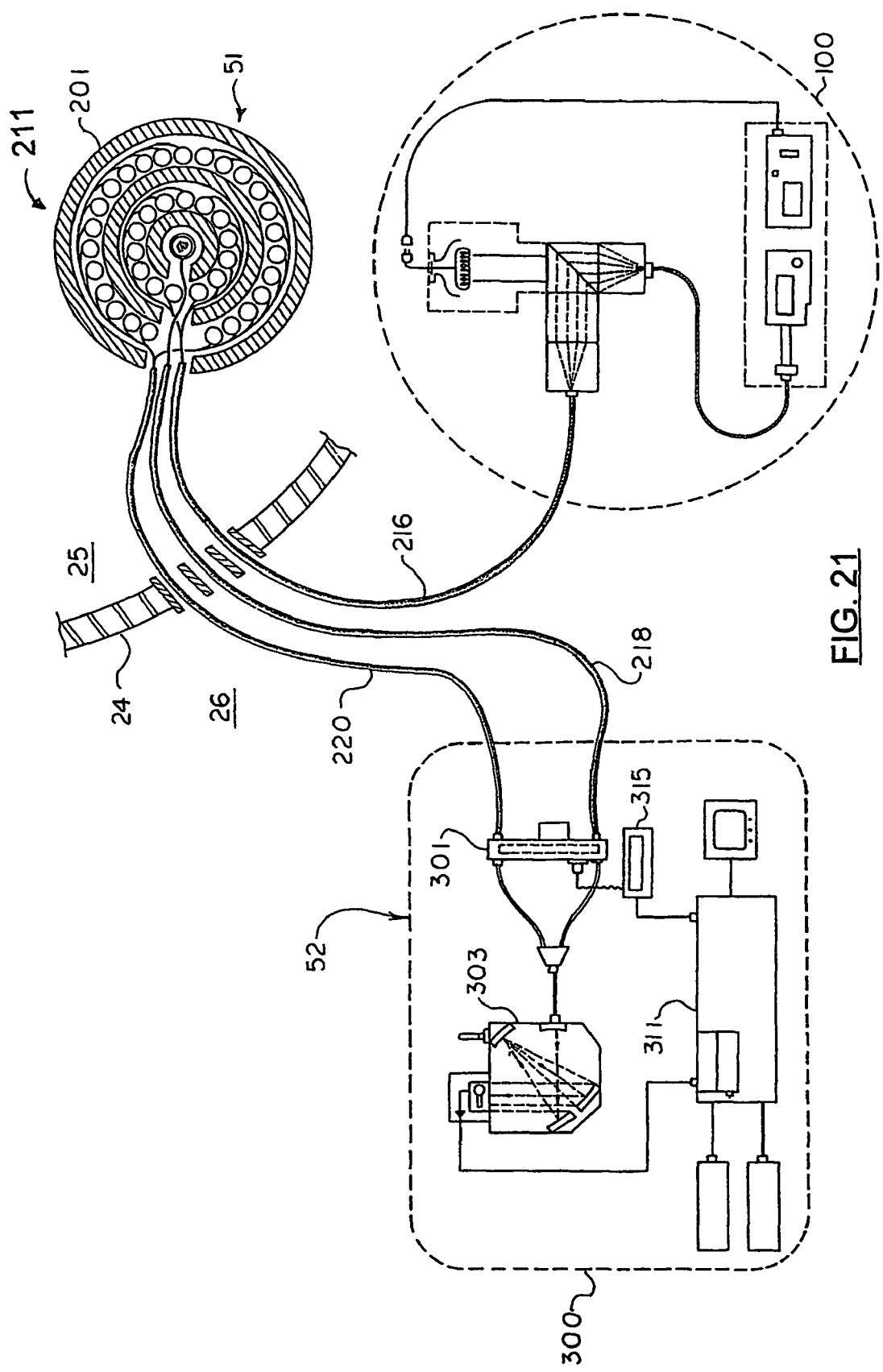
FIG. 21 is a diagram showing how the various features of the present invention are interconnected.
Figure 22:
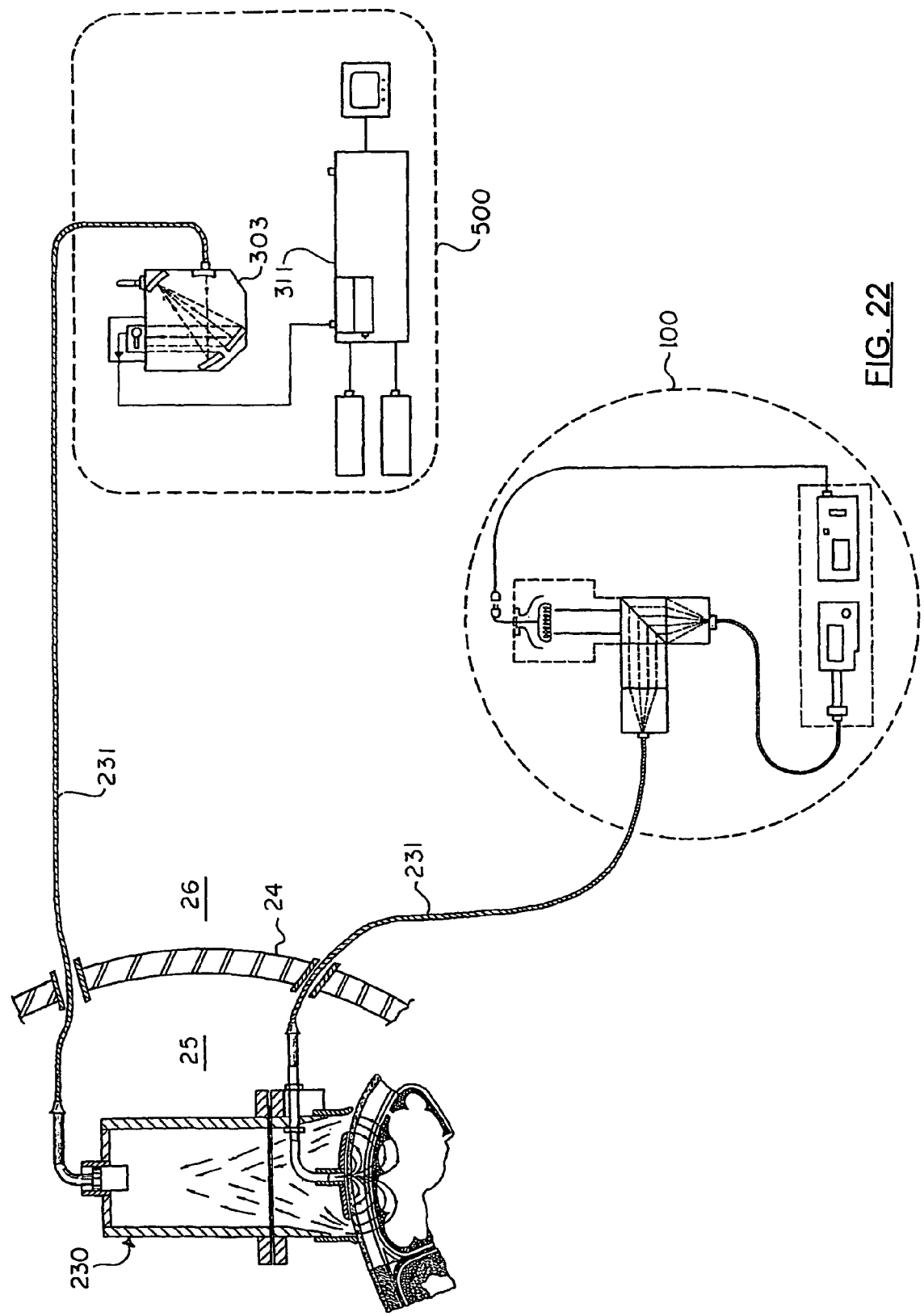
FIG. 22 is a diagram showing alternate features of present unit without real time background measurement using the Fresnel pickup unit.

The NIRoscope 51 and 52 is shown in FIGS. 12 through 21 with the total NIRoscopic system shown in FIGS. 21 and 22. The system is composed of a stabilized near infrared (NIR) light source 100 (FIG. 12) which includes a stabilized power supply 110, Quartz Tungsten Halogen light element 102, a parabolic light collector 111, a hot mirror 105 which eliminates visible and far infrared, and fiber optics light conduit 107. A band pass (600–1100 nm) optical (special order from Oriel) filter can also be used. NIR light is transported via a fiber optics light conduit 216 and introduced into the patient's cranium by the pickup unit 200, 211. The pickup unit 200, 211 can be arranged in a single point mode (FIG. 13) or for maximum NIR light delivery, a ring arrangement (FIGS. 14, 15, and 16) or without background correction (FIG. 17, 18, or 19). Referring back again to FIG. 21, NIR light is delivered to the pickup unit 211/230/250 by fiber optics light conduit 216 through the wall 24 of the chamber 20 to the light input optode 202, traverses through the scalp 205 (see FIG. 13), skull 206, dura matter 207, pia 208, Arachnoid 209 and cerebral cortex 210, and back out again in reverse order via the NIR diffuse light path 212, 213. It has been theoretically predicted by Bonner and experimentally validated by McCormick that the depth of light penetration into the cranium is a function of optode spacing. An optode spacing of 5 cm has been found to be necessary to reach the cerebral cortex. Background pickup optode/ring 203 is located at a distance of approximately 3 cm. This distance is adequate to receive photons that have traversed the scalp and skull but not deep enough to reach the cerebral cortex. The sample pickup optode 204 is positioned to receive photons that have traversed the scalp, skull dura matter, and pia. Subtraction of the background signal from the sample signal results in only the signal representing the cerebral cortex. Absorption spectroscopy requires that the initial light source spectrum be subtracted from the measured light spectrum after traversing through the tissue. The source absorbance spectrum emanating from the cerebral cortex can be highlighted by subtracting any absorbance due to the overlying tissues (i.e., scalp, skull, etc.), from the spectrum measured at pickup optode 204. The spectrum from the signal pickup optode 204 and the background pickup optode 203 are routed to the dual wave interval spectrophotometer 300 by fiber optic conduits 218, 220 (FIG. 20). Both signals are received by a optical chopper 301 where they are presented to the charge-coupled device 307 in sequence via an aperture 304 and optical grading 306. It should be noted that electronic shutters (made by Newport model 845 HP) could replace the optical chopper of low light level applications where needed. The optical grading 306 spreads the spectrum out over the CCD in such a manner that the photon spectra is converted into an electronic spectra which is amplified by amplifier 308 and converted into a digital signal by A/D converter 309 and digitally stored by digital data storage unit 312. Proper sequencing and timing is performed by clock driver 315.

Figure 23:
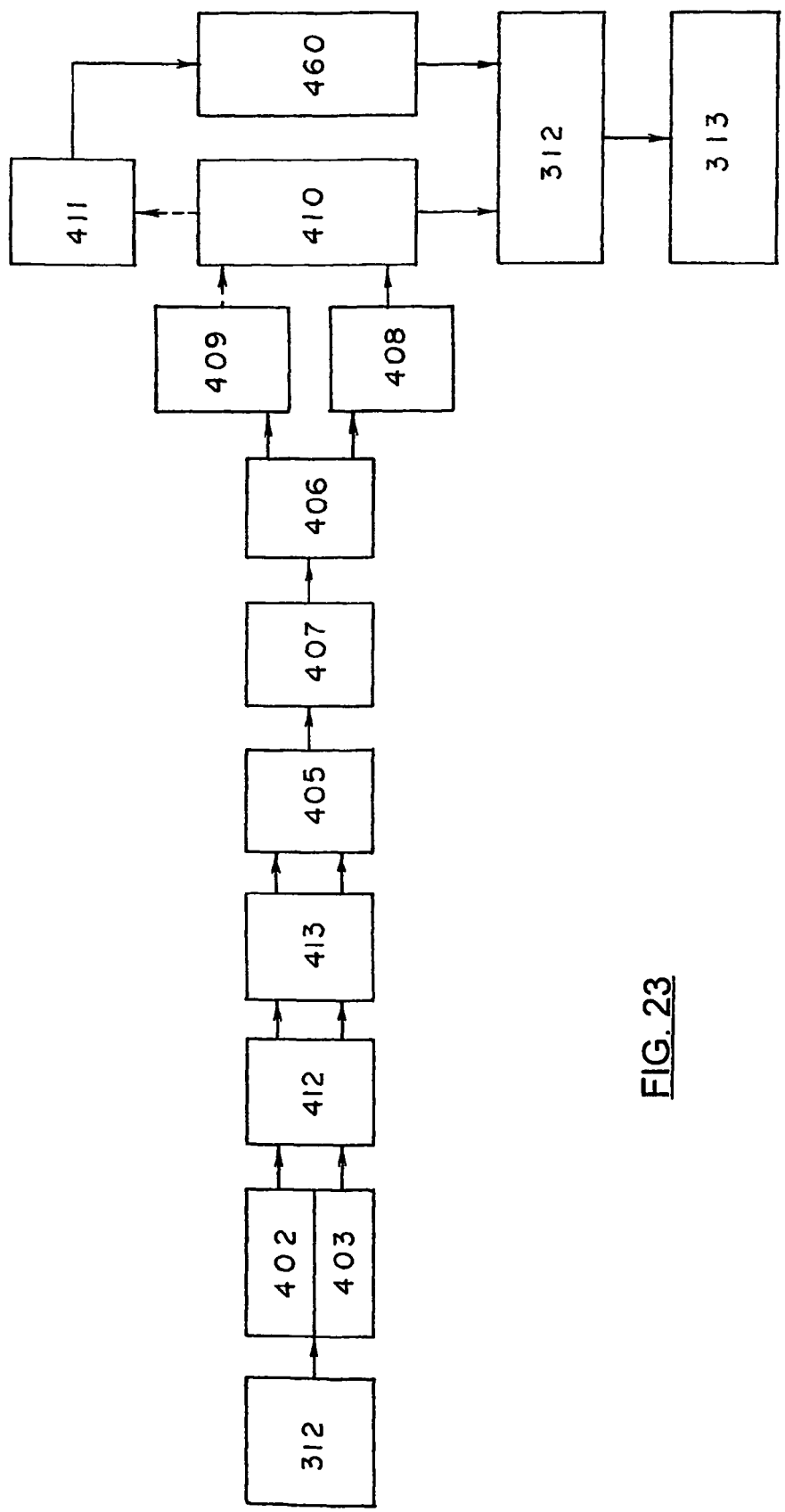
FIG. 23 is a software logic diagram (with real time background measurement).

In memory digital data storage unit 312, two data streams are stored (i.e. sample and background spectra) (see FIG. 23). Data storage unit 312 has available real time alternating background spectra 402 and real time alternating sample spectra 403. All noise pixels are corrected in all spectra 412 and smoothed by Sav-Golay smoothing function ($2^{nd}$ degree polynomial with 51 points) 405. A difference absorption spectrum is then calculated 413 using each pair of background 402 and sample 403 spectrum. An example of calculated difference absorption spectrum 3 is shown in FIG. 1. Next, the dc component of the difference spectrum 3 is removed by integrating the spectrum 3 over the wave length span 400 to 1100 nm, calculating the average wavelength adjustment by dividing the result of the integral by the wave length span interval, and then subtracting the resultant from each wave length absorbance value in the wave length span. An example of absorbance spectrum with DC component removed 5 is in FIG. 2. At this point the Fourier window 406 will be established. The Fourier window is the wave length interval about which the Fourier transform will be taken. It can be a general window which will separate each chromophore (i.e. oxidized and reduced cytochrome oxidase, oxyhemoglobin, deoxyhemoglobin, and water) into specific harmonic components, or a window for each chromophore can be established. At this point a Fourier transform 408 of the spectrum is computed resulting in values for each chromophore. As an alternate, Fourier deconvolution analysis 409 may be used if a more accurate indices of chromophore change is resulted. The resulting indices (for change in oxidized and reduced cytochrome oxidase, oxyhemoglobin and deoxyhemoglobin, and water) are stored 410 in data storage unit 312. These values may be displayed directly on monitor 313 as a function of time start of data acquisition or summed 411 and applied 460 to correct the cytochrome oxidase indices if the absorbance peaks are found to be interdependent.

Figure 7:
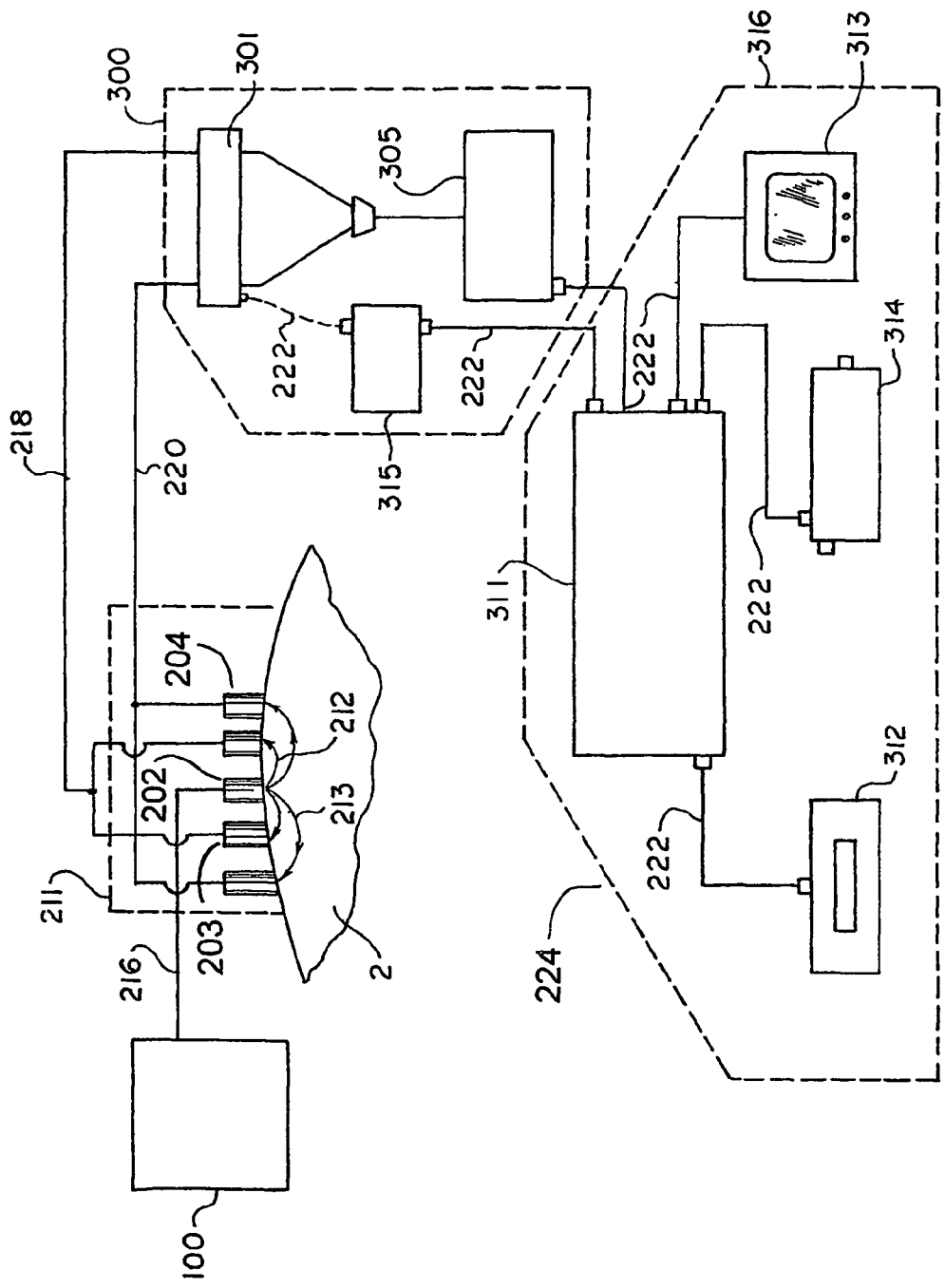
FIG. 7 is a schematic diagram of the NIRoscope of the present invention.
Figure 24:
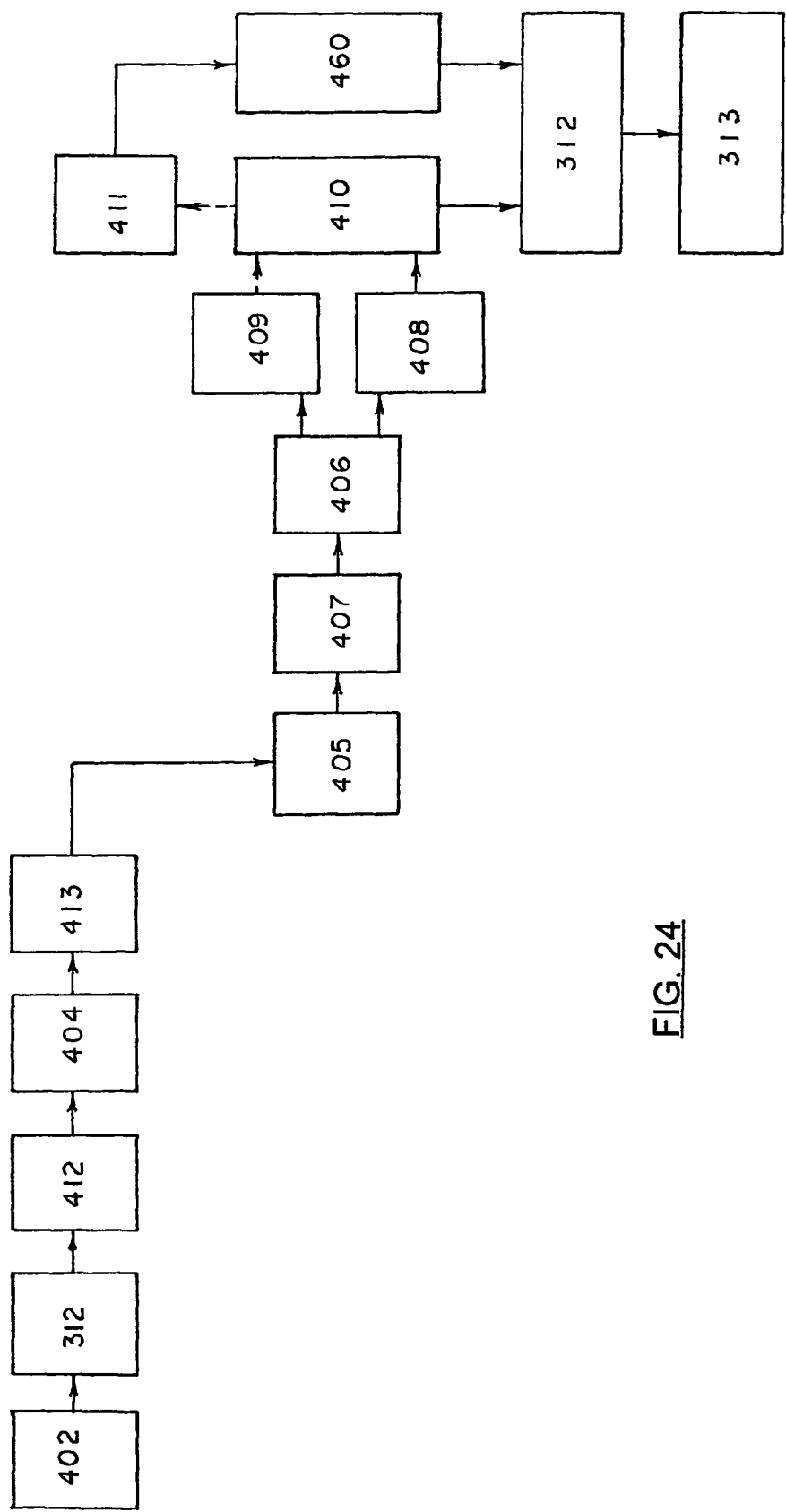
FIG. 24 is a software logic diagram (without real time background measurement).

An alternate simplified method shown in FIG. 24 is as follows. Rather than taking background spectra alternately with sample spectra, a single background spectrum is established before any sample spectrum is taken. Immediately after setup, a series of twenty spectra 418 are taken (for example with 6 second exposure and 4 second interval) and stored in data storage unit 312. Individual noise pixels are corrected 412. These twenty spectra are averaged 404 resulting in one average spectrum. The average spectrum is used as a constant background spectrum for the absorbance calculation of all subsequent sample spectra. All other steps remain the same as in FIG. 23. This technique allow a less complicated arrangement as shown in FIG. 8 verses the more complex arrangement shown in FIG. 7.

All processing is preferably done in Pentium computer 311, with Galatic-Gram 32 software.

All of this equipment is commercially available in the form of a personal computer and a CCD spectrophotometer made by Oriel Inc.

All optical equipment used with the present invention is preferably from Oriel Inc. All control software is preferably from National Instrument and analytical software is preferably Grams 32 from Galatic and Igor. The computer is preferably a standard Pentium.

All measurements disclosed herein are at standard temperature and pressure, at sea level on Earth, unless indicated otherwise. All materials used or intended to be used in a human being are biocompatible, unless indicated otherwise.

APPENDIX OF REFERENCES

1. Virtis, M. Cost/Benefit analysis of cardiopulmonary resuscitation: a comprehensive study-Part II. *Nursing Management* 23(4): 50–54, 1992.
2. Ebell, M. & Kruse, J. A proposed model for the cost of cardiopulmonary resuscitation. *Medical Care* 32(6): 640–649, 1994.
3. Safar, P. Cerebral resuscitation after cardiac arrest: research initiatives and future directions. *Ann of Emerg Med* 22(2): 2324–2349.
4. Holbach, L., et al. Differentiation between reversible and irreversible post-stroke changes in brain tissue: its relevance for cerebrovascular surgery. *Surg Neurol*, 7: 325–331, 1977.
5. Iwatsuki, N., et al. Hyperbaric oxygen combined with nicardipine administration accelerates neurologic recovery after cerebral ischemia in a canine model. *Critical Care Medicine*, 22(5): 858–863, 1994.

6. Van Meter, K, Gottlieb, S., & Whidden, S. Hyperbaric oxygen as an adjunct in ACLS on Guinea pigs after 15 minutes of cardiopulmonary arrest. *Undersea Biomedical Research,* 15(Suppl): 55–56, 1988.
7. Neubauer, R. Gottlieb, S. Enhancing "idling neurons." *Lancet* 335: 542, 1990.
8. Neubauer, R., Gottlieb, S., & Miale, A. Identification of hypometabolic areas in the brain using brain imaging and hyperbaric oxygen. *Clinical Nuclear Medicine* 17: 477–481, 1992.
9. Neubauer, R. Gottlieb, S., Pevsner, H. Hyperbaric oxygen for treatment of closed head injury. *Southern Medical Journal* 84(9): 933–936, 1994.
10. Waxman, K., Annas, C., Daughters, K., et al. A method to determine the adequacy of resuscitation using tissue oxygen monitoring. *Journal of Trauma* 36(6): 852–857.
11. Rivers, E., Martin, G., et al. The clinical implications of continuous central venous oxygen saturation during human CPR. *Annals of Emergency Medicine* 21: 1094–1101, 1992.
12. McCormick, P., Stewart, G., et al. Measurement of human hypothermic cerebral oxygen metabolism by transmission spectroscopy. Advances in experimental medicine and biology 333: 33–41, 1993.
13. Jobsis, F., Piantadosi, G. et al. Near infrared monitoring of cerebral oxygen sufficiency. *Neuro Resea* 10: 7–17, 1988.
14. Brazy, J. & Lewis, D. Changes in cerebral blood volume and cytochrome aa3 during hypertensive peaks in pre-term infarcts 108: 983–987, 1986.
15. Glaister, D., Jobsis, F. A near infrared spectrophotometric method for studying brain $O_2$ sufficiency in man during +$G_z$ acceleration. *Aviation, Space and Environmental Medicine* 59(3): 199–207, 1988.
16. Cope, M. et al. System for long term measurement of cerebral blood and tissue oxygenation on newborn infants by near infrared translumination. Med and Biol Eng Comp 26: 289–294, 1988.
17. Hoshi, Y. Et al. Oxygen dependence of redox state of copper in cytochrome oxidase in vitro. *J App Phys* 74(9): 1622–1627, 1993.
18. Wray, S., et al. Characterization of near infrared absorption spectra of cytochrome aa3 and hemoglobin for the non-invasive monitoring of cerebral oxygenation, Bioch and Biophy Acta 933: 918–929, 1987.
19. Adkisson G H, Hodgson M, Smith F, Torok Z, Macleon M A, Sykes J J W, Strack C, Pearson R R, Cerebral perfusion deficits in dysbaric illness, The Lancet, 2, 119–121, 1989.
20. Matcher S, Elwell C, Cooper E, Cope M, Delpy D. Performance comparison of several published tissue near-infrared spectroscopy algorithms. Analytical Biochemistry 1995; 227: 54–68.
21. Miyake H., Nioda S., Zaman A., Smith D., Chance B. The detection of cytochrome oxidase, Heme Iron, and Copper Absorption in blood perfused and blood free brain in Normoxia and Hypoxia Analytical Biochemistry 1991; 192: 149–155.

Incorporated herein by reference is the paper entitled "Cytochrome oxidase reduction/oxidation charge coupled monitor with large area pickup optode" and reproduced on the following pages 30–43, which describes results of the invention of the present inventors applied to a swine model.

The foregoing embodiments are presented by way of example only; the scope of the present invention is to be limited only by the following claims.

What is claimed is:

1. A system comprising:
   (a) a light source;
   (b) a pickup optode unit for detecting light from the light source;
   (c) a spectrophotometer coupled to the pickup optode unit for sensing and recording a NIR wavelength interval including cytochrome oxidase, water and hemoglobin data;
   (d) a personal computer with a software algorithm to extract via model-free mathematical operations the cytochrome oxidase, water and hemoglobin data from the NIR wavelength interval for evaluation and display.

2. The system of claim 1, wherein the light source is a stabilized pulsed light.

3. A method of using the system of claim 1 to monitor the change of any natural or manmade chromophore existing in a person's brain to assist in the diagnosis or treatment of a neurological or psychotic disorder, comprising:
   using the light source to illuminate a person's cerebral tissue;
   using the pickup optode unit to detect light from the person's cerebral tissue;
   using the spectrophotometer to sense and record a NIR wavelength interval including cytochrome oxidase, water and hemoglobin data;
   using the personal computer and the software algorithm to extract the cytochrome oxidase, water and hemoglobin data from the NIR wavelength interval for evaluation.

4. The method of claim 3, wherein the light source is a stabilized pulsed light.

5. The method of claim 3, wherein the spectrophotometer monitors relative changes in redox levels in real-time.

6. The method of claim 3, wherein Fourier transforms are used in analyses of near infrared data obtained from the spectrophotometer.

7. The method of claim 3, wherein:
   the spectrophotometer includes:
     a background pickup device which receives photons that have traversed the patient's scalp and skull but not deep enough to reach the patient's cerebral cortex,
     a sample pickup device that is positioned to receive photons that have traversed the patient's scalp, skull dura matter, and pia, and
   the background signal is subtracted from the sample signal by the algorithm to result in a signal representing the patient's cerebral cortex.

8. The method of claim 3, wherein the light source is a quartz halogen 150 watt light source.

9. The method of claim 3, wherein the NIR wavelength interval is about 700–1050 nm.

10. The method of claim 3, wherein oxygen in cerebral tissue is monitored by monitoring cytochrome oxidase in the cerebral tissue.

11. The method of claim 3, wherein oxygen in cerebral tissue is monitored by monitoring the redox ratio of cytochrome oxidase in the patient's cerebral tissue.

12. The invention of claim 1, wherein the spectrophotometer monitors relative changes in redox levels in real-time.

13. The invention of claim 1, wherein the software algorithm uses Fourier transforms in analyses of near infrared data obtained from the spectrophotometer.

14. The invention of claim 1, wherein:
the spectrophotometer includes:
- a background pickup device which receives photons that have traversed a patient's scalp and skull but not deep enough to reach the patient's cerebral cortex,
- a sample pickup device that is positioned to receive photons that have traversed the patient's scalp, skull dura matter, and pia, and
the background signal is subtracted from the sample signal by the software algorithm to result in a signal representing the patient's cerebral cortex.

15. The system of claim 1, wherein the light source is a quartz halogen 150 watt light source.

16. The system of claim 1, wherein the NIR wavelength interval is about 700–1050 nm.

17. The invention of claim 1, comprising means for monitoring oxygen in cerebral tissue by monitoring cytochrome oxidase in a patient's cerebral tissue.

18. The invention of claim 1, comprising means for monitoring oxygen in cerebral tissue by monitoring the redox ratio of cytochrome oxidase in the cerebral tissue.

19. The system of claim 1, further comprising connecting fiber optics attached to the light source.

20. The system of claim 19, further comprising a near infrared band pass filter and wherein the spectrophotometer is a dual wave interval spectrophotometer.

21. The system of claim 1, further comprising a near infrared band pass filter.

22. The system of claim 1, wherein the spectrophotometer is a dual wave interval spectrophotometer.

* * * * *